(12) United States Patent
Watanabe

(10) Patent No.: US 10,952,616 B2
(45) Date of Patent: Mar. 23, 2021

(54) FLUORESCENCE IMAGING APPARATUS

(71) Applicant: Canon U.S.A., Inc., Melville, NY (US)

(72) Inventor: Kohei Watanabe, Brookline, MA (US)

(73) Assignee: Canon U.S.A., Inc., Melville, NY (US)

( * ) Notice: Subject to any disclaimer, the term of this patent is extended or adjusted under 35 U.S.C. 154(b) by 25 days.

(21) Appl. No.: 16/368,510

(22) Filed: Mar. 28, 2019

(65) Prior Publication Data

US 2019/0298174 A1    Oct. 3, 2019

Related U.S. Application Data

(60) Provisional application No. 62/650,658, filed on Mar. 30, 2018, provisional application No. 62/799,516, filed on Jan. 31, 2019.

(51) Int. Cl.
    *A61B 5/00*      (2006.01)
    *G01N 21/47*      (2006.01)

(52) U.S. Cl.
    CPC .......... *A61B 5/0066* (2013.01); *A61B 5/0071* (2013.01); *A61B 5/0075* (2013.01); *G01N 21/4795* (2013.01)

(58) Field of Classification Search
    CPC .......... A61B 2560/0223; A61B 5/0066; A61B 5/0071; A61B 5/0075; G01N 21/274; G01N 21/4795; G01N 21/6458
See application file for complete search history.

(56) References Cited

U.S. PATENT DOCUMENTS

| | | |
|---|---|---|
| 5,046,501 A | 9/1991 | Crilly |
| 5,106,387 A | 4/1992 | Kittrell et al. |
| 5,303,026 A | 4/1994 | Strobl et al. |
| 5,419,323 A | 5/1995 | Kittrell et al. |
| 5,439,000 A | 8/1995 | Gunderson et al. |
| 5,452,723 A | 9/1995 | Wu |
| 5,562,100 A | 10/1996 | Kittrell et al. |
| 5,697,373 A | 12/1997 | Richards-Kortum et al. |
| 6,002,137 A | 12/1999 | Hayashi |
| 6,026,319 A | 2/2000 | Hayashi |
| 6,070,096 A | 5/2000 | Hayashi |
| 6,095,982 A | 8/2000 | Richards-Kortum et al. |

(Continued)

FOREIGN PATENT DOCUMENTS

| | | |
|---|---|---|
| JP | 2015532179 A | 11/2015 |
| JP | 2016099253 A | 5/2016 |

OTHER PUBLICATIONS

Ughi et al. ("Dual modality intravascular optical coherence tomography (OCT) and near-infrared fluorescence (NIRF) imaging: a fully automated algorithm for the distance-calibration of NIRF signal intensity for quantitative molecular imaging", Int J Cardiovasc Imaging, 31, p. 259-268, 2015) (Year: 2015).*

(Continued)

*Primary Examiner* — Hina F Ayub

(74) *Attorney, Agent, or Firm* — Canon U.S.A., Inc. IP Division

(57) ABSTRACT

A method of fluorescence calibration. An excitation light is provided and incident on an object through an optical probe. The fluorescence light generated from the object is detected. Structural data of the object is acquired, and an optical attenuation property of the object is calculated based on the structural data. The fluorescence intensity is then calibrated based on the optical attenuation property.

17 Claims, 16 Drawing Sheets

(56) References Cited

U.S. PATENT DOCUMENTS

| | | | |
|---|---|---|---|
| 6,317,624 B1 | 11/2001 | Kollias et al. | |
| 6,465,968 B1 | 10/2002 | Sendai | |
| 6,516,217 B1 | 2/2003 | Tsujita | |
| 6,574,502 B2 | 6/2003 | Hayashi | |
| 6,697,657 B1 | 2/2004 | Shehada et al. | |
| 6,763,261 B2 | 7/2004 | Casscells, III et al. | |
| 6,780,182 B2 | 8/2004 | Bowman et al. | |
| 6,800,057 B2 | 10/2004 | Tsujita et al. | |
| 6,869,593 B2 | 3/2005 | Frangioni | |
| 6,915,154 B1 | 7/2005 | Docherty et al. | |
| 7,113,814 B2 | 9/2006 | Ward et al. | |
| RE39,672 E | 6/2007 | Shehada et al. | |
| 7,366,376 B2 | 4/2008 | Shishkov et al. | |
| 7,428,048 B1 | 9/2008 | Farkas et al. | |
| 7,447,408 B2 | 11/2008 | Bouma et al. | |
| 7,449,153 B2 | 11/2008 | Sakai et al. | |
| 7,483,554 B2 | 1/2009 | Kotsianti et al. | |
| 7,508,524 B2 | 3/2009 | Mahadevan-Jansen et al. | |
| 7,587,236 B2 | 9/2009 | Demos et al. | |
| 7,749,168 B2 | 7/2010 | Maschke et al. | |
| 7,843,572 B2 | 11/2010 | Tearney et al. | |
| 7,872,759 B2 | 1/2011 | Tearney et al. | |
| 7,877,135 B2 | 1/2011 | Iketani et al. | |
| 7,889,348 B2 | 2/2011 | Tearney et al. | |
| 7,890,157 B2 | 2/2011 | Jo et al. | |
| 7,952,706 B2 | 5/2011 | Ling et al. | |
| 7,952,719 B2 | 5/2011 | Brennan, III | |
| 8,035,819 B2 | 10/2011 | Zuluaga | |
| 8,084,755 B2 | 12/2011 | Hall et al. | |
| 8,089,625 B2 | 1/2012 | Maruc et al. | |
| 8,219,183 B2 | 7/2012 | Maschke et al. | |
| 8,289,522 B2 | 10/2012 | Tearney et al. | |
| 8,380,268 B2 | 2/2013 | Georgakoudi et al. | |
| 8,473,036 B2 | 6/2013 | Gorman, III et al. | |
| 8,553,219 B2 | 10/2013 | Patil et al. | |
| 8,571,640 B2 | 10/2013 | Holman | |
| 8,582,096 B2 | 11/2013 | Chen et al. | |
| 8,849,380 B2 | 9/2014 | Patwardhan | |
| 8,928,889 B2 | 1/2015 | Tearney et al. | |
| 8,953,911 B1 | 2/2015 | Xu et al. | |
| 9,087,368 B2 | 7/2015 | Tearney et al. | |
| 9,121,926 B2 | 9/2015 | Nair et al. | |
| 9,179,845 B2 | 11/2015 | Farcy et al. | |
| 9,286,673 B2 | 3/2016 | Begin et al. | |
| 9,326,682 B2 | 5/2016 | Tearney et al. | |
| 9,332,942 B2 | 5/2016 | Jaffer et al. | |
| 9,557,154 B2 | 1/2017 | Tearney et al. | |
| 9,795,301 B2 | 10/2017 | Fleming et al. | |
| 9,869,828 B2 | 1/2018 | Altshuler | |
| 10,130,259 B2 | 11/2018 | Lam et al. | |
| 2004/0156782 A1 | 8/2004 | Alam | |
| 2004/0241089 A1 | 12/2004 | Brister et al. | |
| 2005/0273267 A1 | 12/2005 | Maione | |
| 2007/0038124 A1 | 2/2007 | Fulghum, Jr. et al. | |
| 2007/0078348 A1 | 4/2007 | Holman | |
| 2007/0158585 A1* | 7/2007 | Hall | G01N 21/6408 250/458.1 |
| 2007/0225579 A1 | 9/2007 | Lucassen et al. | |
| 2008/0103384 A1 | 5/2008 | Pfister | |
| 2008/0177145 A1 | 7/2008 | Furnish | |
| 2008/0228086 A1 | 9/2008 | Ilegbusi et al. | |
| 2008/0255426 A1 | 10/2008 | Iketani | |
| 2009/0073439 A1 | 3/2009 | Tearney et al. | |
| 2009/0153852 A1 | 6/2009 | Rensen | |
| 2009/0192358 A1 | 7/2009 | Jaffer et al. | |
| 2009/0203991 A1 | 8/2009 | Papaioannou et al. | |
| 2009/0262993 A1 | 10/2009 | Kotsianti et al. | |
| 2010/0092389 A1 | 4/2010 | Jaffer | |
| 2010/0315632 A1 | 12/2010 | Brennan, III | |
| 2011/0237895 A1 | 9/2011 | Yoshida et al. | |
| 2011/0292400 A1 | 12/2011 | Fleming et al. | |
| 2012/0101374 A1 | 4/2012 | Tearney et al. | |
| 2013/0235369 A1* | 9/2013 | Koifman | G01M 11/31 356/73.1 |
| 2014/0276011 A1 | 9/2014 | Schmitt et al. | |
| 2015/0080686 A1 | 3/2015 | Karlheinz et al. | |
| 2015/0141278 A1* | 5/2015 | Hollman-Hewgley | G06T 7/0012 506/9 |
| 2015/0185151 A1 | 7/2015 | Utzinger et al. | |
| 2016/0228097 A1 | 8/2016 | Jaffer et al. | |
| 2017/0135584 A1 | 5/2017 | Tearney et al. | |
| 2017/0209049 A1 | 7/2017 | Wang et al. | |
| 2018/0055953 A1 | 3/2018 | Jaffer et al. | |
| 2018/0136129 A1 | 5/2018 | Rizo et al. | |
| 2018/0348439 A1 | 12/2018 | Yamada | |
| 2019/0059734 A1 | 2/2019 | Yamada | |
| 2019/0391338 A1 | 12/2019 | Tearney et al. | |
| 2020/0085285 A1 | 3/2020 | Yamada | |

OTHER PUBLICATIONS

Ughi, G. J., et al "Dual modality intravascular optical coherence tomography (OCT) and near-infrared fluorescence (NIRF) imaging: a fully automated algorithm for the distance-calibration of NIRF signal intensity for quantitative molecular imaging", Int J Cardiovasc Imaging, Author Manuscript, Feb. 2015, pp. 1-18, vol. 31, No. 2.

Koskinas, K. C., et al., "Intracoronary imaging of coronary atherosclerosis: validation for diagnosis, prognosis and treatment", European Heart Journal, Dec. 2015, pp. 1-15.

Vinegoni, C., et al al, "Indocyanine Green Enables Near-Infrared Fluorescence Imaging of Lipid-Rich, Inflamed Atherosclerotic Plaques", Sci Transl Med, May 25, 2011, vol. 3, No. 84, pp. 1-20.

Osborn, E. A., et al, "The Advancing Clinical Impact of Molecular Imaging in CVD", JACC: Cardiovascular Imaging, Dec. 2013, pp. 1-25, vol. 6, No. 12.

Lee, S., et al, "Fully Integrated High-Speed Intravascular Optical Coherence Tomography/Near-Infrared Fluorescence Structural/Molecular Imaging In Vivo Using a Clinically Available Near-Infrared Fluorescence- Emitting Indocyanine Green to Detect Inflamed Lipid-Rich Atheromata in Coronary-Sized Vessels", Circ Cardivasc Interv, 2014, pp. 560-569.

Hara, T., et al, "Molecular imaging of fibrin deposition in deep vein thrombosis using a new fibrin-targeted near-infrared fluorescence (NIRF) imaging strategy", JACC Cardiovasc Imaging, Jun. 2012, pp. 1-16, vol. 5, No. 6.

Jo, J. A., et al, "Simultaneous morphological and biotechnical endogenous optical imaging of atherosclerosis", European Heart Journal—Cardiovascular Imaging, 2015, pp. 910-918, vol. 16.

Fard, A. M., et al, "Optical coherence tomography—near infrared spectroscopy system and catheter for intravascular imaging", Optics Express, Dec. 16, 2013, pp. 30849-30858 vol. 21, No. 25.

Phipps, J., et al, "Fluorescence lifetime imaging for the characterization of the biochemical composition of atherosclerotic plaques", Joural of Biomedical Optics, Sep. 2011, vol. 16, No. 9, pp. 096018-1-096018-8.

Scepanovic, O. B., et al, "Multimodal spectroscopy detects features of vulnerable atherosclerotic plaque", Journal of Biomedical Optics, Jan. 2011, vol. 16, No. 1, pp. 011009-1-011009-10.

Ughi, G. J., et al, "Clinical Characterization of Coronary Atherosclerosis With Dual-Modality OCT and Near-Infrared Autofluorescence Imaging", JACC Cardiovascular Imaging, 2016, pp. 1-11.

Yoo, H., et al, "Intra-arterial catheter for simultaneous microstuctural and molecular imaging in vivo", Nature Medicine, Dec. 2011, pp. 1680-1685, vol. 17, No. 12.

Sebastian Dochow, et al., Combined Fiber Probe for Fluorescence Lifetime and Raman Spectroscopy, Author manuscript, Anal Bioanal Chem., PMC, Aug. 23, 2016, pp. 1-20.

Jessica P. Miller, et al., Noninvasive Depth Estimation Using Tissue Optical Properties and a Dual-Wavelength Fluorescent Molecular Probe in Vivo, Biomedical Optics Express, Jun. 1, 2017, pp. 3095-3109, vol. 8, No. 6.

Hao Wang, et al., Ex Vivo Catheter-Based Imaging of Coronary Atherosclerosis Using Multimodality OCT and NIRAF Excited at 633 nm, Biomedical Optics Express, Mar. 19, 2015, pp. 1363-1375, vol. 6, No. 4.

(56) References Cited

OTHER PUBLICATIONS

Dinglong MA, et al. Rotational Multispectral Fluorescence Lifetime Imaging and Intravascular Ultrasound: Bimodal System for Intravascular Applications, Journal of Biomedical Optics, vol. 19, Issue 6, Jun. 2014, 12 pages.

AJ Dixon, et al., Intravascular near-infrared fluorescence catheter with ultrasound guidance and blood attenuation correction. Journal of Biomedical Optics, May 2013, vol. 18, No. 5, 11 pages.

Shengnan Liu, et al., Analysis and compensation for the effect of the catheter position on image intensities in intravascular optical coherence tomography, Journal of Biomedical Optics, Dec. 2016, vol. 21, No. 12, 10 pages.

Loretta Scolaro, et al., "Molecular Imaging Needles: Dual-Modality Optical Coherence Tomography and Fluorescence Imaging of Labeled Antibodies Deep in Tissue", Biomedical Optics Express, Optical Society of America, vol. 6, No. 5, May 2015, pp. 1767-1781.

Wang, H., "Near infrared autofluorescence augmentation of optical coherence tomography for diagnosis of coronary atherosclerosis", Thesis/Dissertation, Boston University College of Engineering, 2014, 251 pages.

\* cited by examiner

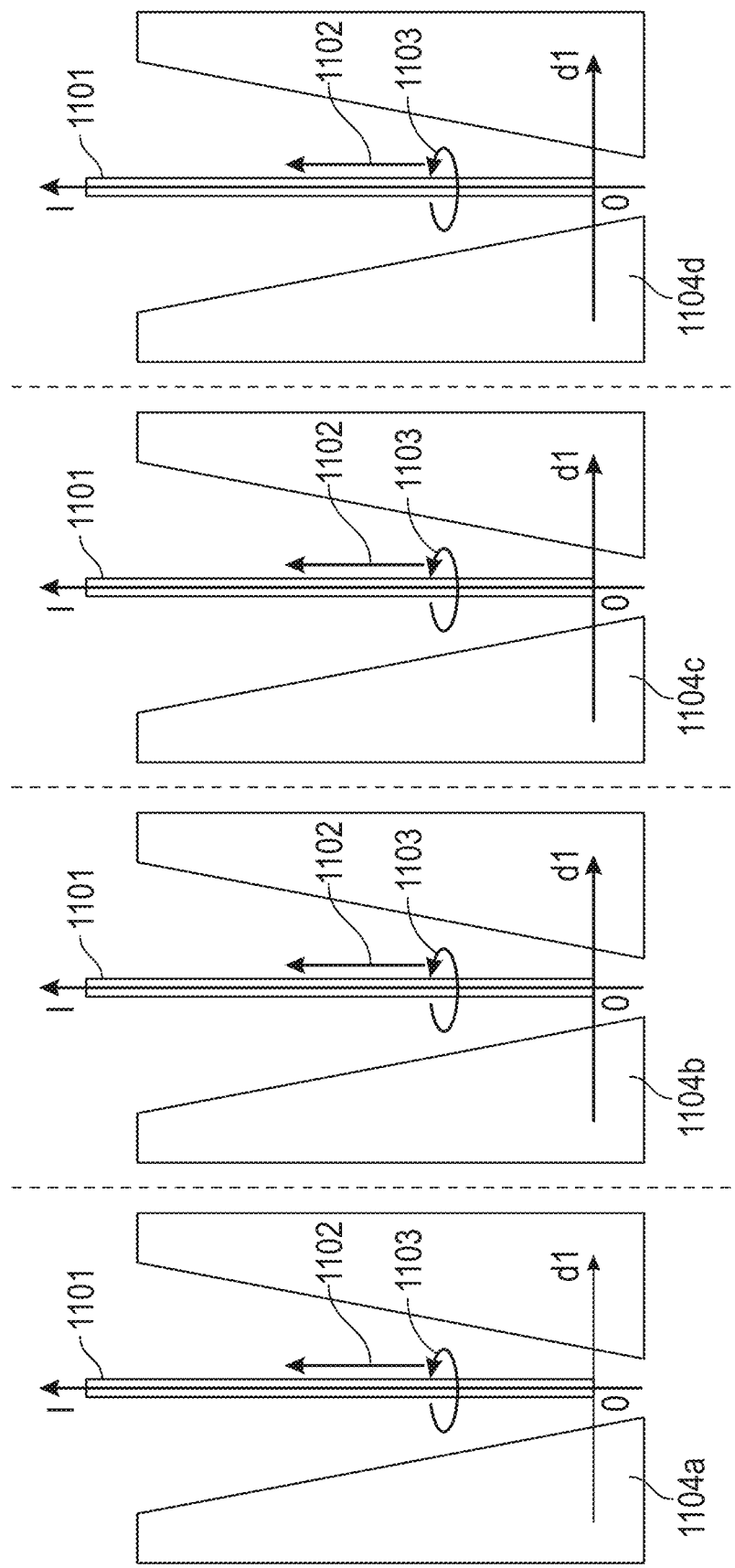

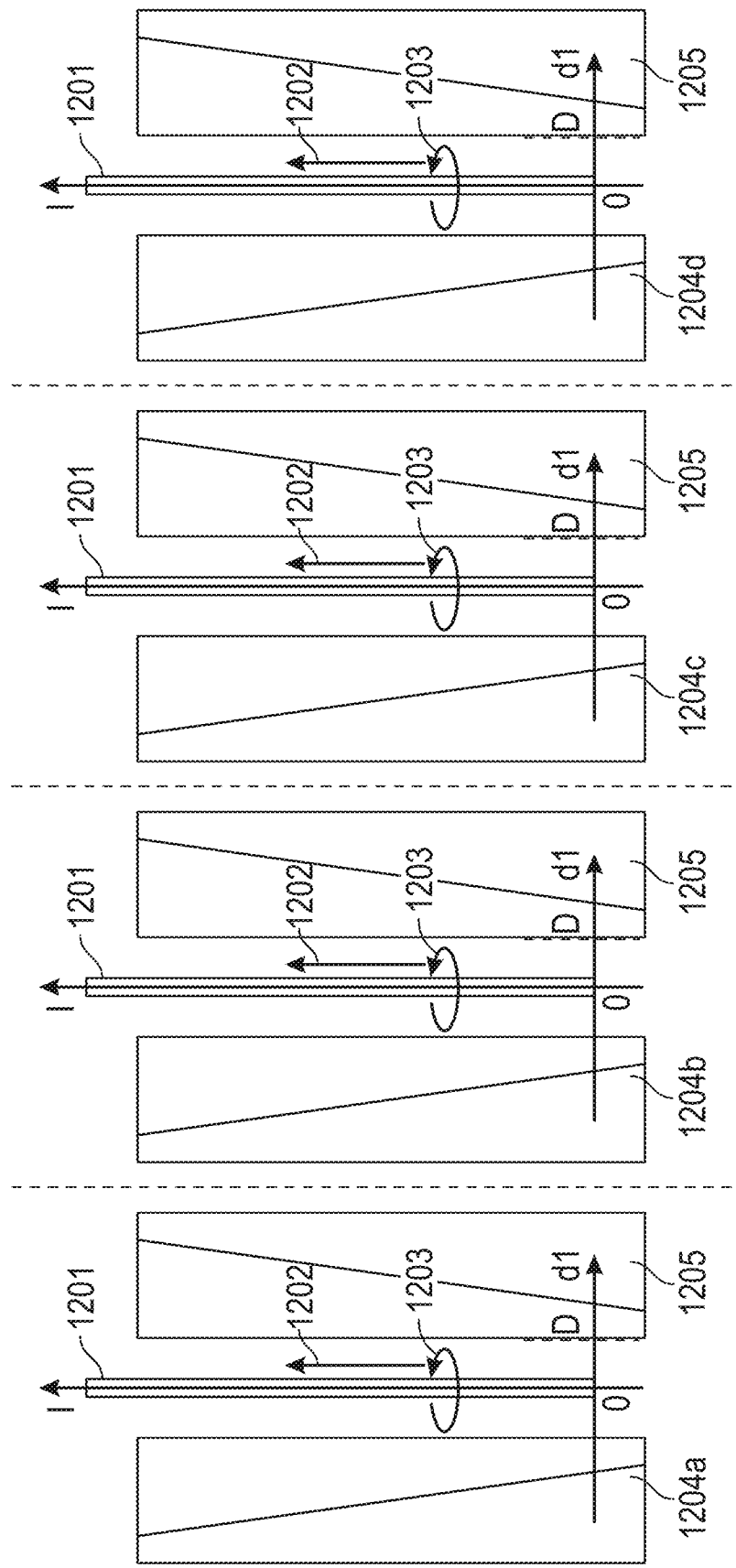

| | | Multiple Layers | | | Single Layers | |
|---|---|---|---|---|---|---|
| | | Non-Fluorescence Layer on Top | Fluorescence Layer on Top | Non-Fluorescence Layers Only | Fluorescence Layer | Non-Fluorescence Layer |
| Distance Correction for Inner Area of the Vessel | (Option 1) Single Correction Function | Distance corr.: Normal  Depth corr.: the corr. Function is Determined for the Top Layer | Distance corr.: Normal  Depth corr.: n/a | No Distance/Depth Correction Performed | Distance corr.: Normal  Depth corr.: n/a | No Distance/Depth Correction Performed |
| | (Option 2) 1st-Layer-Dependent Correction Functions | Distance corr.: the corr. Function is Determined Based on the Top Layer  Depth corr.: the corr. Function is Determined for the Top Layer | Distance corr.: the corr. Function is Determined for the Fluorescence Layer  Depth corr.: n/a | No Distance/Depth Correction Performed | Distance corr.: the corr. Function is Determined for the Fluorescence Layer  Depth corr.: n/a | No Distance/Depth Correction Performed |

FIG. 16

FLUORESCENCE IMAGING APPARATUS

CROSS REFERENCE TO RELATED APPLICATIONS

This application claims priority from U.S. Provisional Patent Application No. 62/650,658 filed on Mar. 30, 2018, in the United States Patent and Trademark Office, as well U.S. Provisional Patent Application No. 62/799,516 filed on Jan. 31, 2019, in the United States Patent and Trademark Office, the disclosures of both being incorporated by reference herein in their entirety.

BACKGROUND

Field of the Disclosure

The present disclosure relates in general to a fluorescence imaging apparatus, and more particularly, to an integration of optical coherence tomography (OCT) and fluorescence spectroscopy.

Description of the Related Art

Optical coherence tomography (OCT) provides high-resolution, cross-sectional imaging of tissue microstructure in situ and in real-time, while fluorescence imaging enables visualization of molecular processes. The integration of OCT and fluorescence imaging in a single catheter provides the capability to simultaneously obtain co-localized anatomical and molecular information from a tissue such as the artery wall. For example, in "*Ex. Vivo catheter-based imaging of coronary atherosclerosis using multimodality OCT and NIRAF excited at 633 nm*" (Biomed Opt Express 2015, 6(4): 1363-1375), Wang discloses an OCT-fluorescence imaging system using He:Ne excitation light for fluorescence and swept laser for OCT simultaneously through the optical fiber probe. Usually, in optical imaging, the signal strength can depend on the distance. The fluorescence signal is weaker when the distance from the imaging probe to the sample is farther. The system disclosed by Wang calibrates the fluorescence light intensity detected by an optical fiber using distance between the optical fiber and the tissue, while OCT can measure the distance. However, it is found that the collection efficiency of fluorescence by an optical fiber depends not only the distance between the optical fiber and the tissue, but also an optical property such as optical attenuation property or scattering property of tissue.

SUMMARY

The present patent application aims to improve the accuracy of the fluorescence imaging by a fluorescence calibration method that incorporates the optical property of the fluorescence sample. In one embodiment, an excitation light is provided and incident on an object through an optical probe. The fluorescence light generated from the object is detected. Structural data of the object is acquired. An optical attenuation property of the object is calculated based on the structural data. The fluorescence intensity is then calibrated based on the optical attenuation property.

Preferably, a distance between optical probe and the object is also calculated and the fluorescence intensity is calibrated based on the distance and the optical attenuation property. Preferably but optionally, the fluorescence intensity and the structural data are obtained simultaneously. The fluorescence light and the structural data may be delivered by a double clad fiber, such that the structural data is delivered by a core of the double clad fiber, and the fluorescence light is delivered by a cladding of the double clad fiber. The fluorescence light may include a near-infrared light. The method of fluorescence calibration may further comprise acquiring the structural data by optical coherence tomography. The optical attenuation property includes attenuation coefficient of an OCT image. The fluorescence intensity is then calibrated and fluorescence image is constructed. In another embodiment, a method of fluorescence calibration further includes the steps of; calculating an optical attenuation property of at least the top layer of the object if the object has heterogeneous optical property, calculating the depth of at least the top layer. The fluorescence intensity is then calibrated based on the distance, optical attenuation property and the depth. Then fluorescence image is constructed.

In another embodiment, a method of fluorescence calibration including the following steps is provided. An excitation light is provided and incident on an object through an optical probe. The fluorescence intensity of the fluorescence light generated from the object is detected. Structural data of the object is acquired. A distance between the optical probe and the object is calculated. The fluorescence intensity is calibrated based on the distance. If the fluorescence intensity calibrated based on the distance is higher than a predetermined level, an optical attenuation property of the object is acquired based on the structural data. The fluorescence intensity of the fluorescence light is further calibrated based on the optical attenuation property. In another embodiment, an optical attenuation property of the object is acquired based on the structural data and the fluorescence intensity of the fluorescence light is calibrated based on the optical attenuation property. If the fluorescence intensity calibrated based on the optical attenuation property is higher than a predetermined level, a distance between the optical probe and the object is calculated. The fluorescence intensity of the fluorescence light is further calibrated based on the distance.

The method may further comprise obtaining the fluorescence intensity and the structural data simultaneously. The fluorescence light and the structural data may be delivered by a double clad fiber. The structural data is delivered by a core of the double clad fiber, and the fluorescence light is delivered by a cladding of the double clad fiber. The fluorescence light includes a near-infrared light. The method may further comprise acquiring the structural data by optical coherence tomography (OCT). The optical attenuation property includes attenuation coefficient of an OCT signal in the object. The calibrated fluorescence is then applied for correcting a fluorescence image constructed by the fluorescence light.

If the fluorescence intensity calibrated by the first calibration factor is not higher than the predetermined level, only the fluorescence intensity calibrated by the first calibration factor is applied for correcting a fluorescence image constructed by the fluorescence light. If the fluorescence intensity calibrated by the first calibration factor is higher than the predetermined level, the fluorescence intensity further calibrated by the second calibration factor is applied for correcting a fluorescence image constructed by the fluorescence light. For calibrating the fluorescence intensity using both the first and the second calibration factor, the second calibration factor can be applied to the fluorescence intensity calibrated with the first calibration factor or the third calibration factor that is calculated from the first and the second calibration factor can be applied to the original fluorescence intensity.

A fluorescence imaging system is also provided. The system includes a light source configured to generate an excitation light, an optical waveguide to guide the excitation light toward an object and to detect fluorescence light generated by the object in response to the excitation light, an OCT system configured to obtain an OCT image from the object, and a signal processor. The signal processor comprises an OCT image processing unit and a fluorescence processing unit. The OCT image processing unit is configured to calculate a distance between the catheter and the object and a attenuation coefficient. The fluorescence processing unit is configured to i) calibrate fluorescence intensity of the fluorescence light based on the distance and the attenuation coefficient; or ii) calibrate fluorescence intensity of the fluorescence light based on the distance, and if the fluorescence intensity calibrated based on the distance is higher than a predetermined level, calibrate the fluorescence light based on the attenuation coefficient.

The distal end of the optical waveguide may be configured to direct light to and collect light from a side angle. The system may further comprise a rotation unit that rotates the optical waveguide.

The system may further comprise a pullback unit for scanning the sample during the imaging. A double clad fiber may be used for delivering the fluorescence light and OCT image. The fluorescence light can be delivered by a cladding of the double clad fiber and the OCT image can be delivered by a core of the double clad fiber.

The subject disclosure further teaches a method for correcting fluorescence data measurements, comprising: defining a border between a first layer and a second layer of a subject structure; calculating a depth of the second layer; calculating a depth calibration factor by plugging in a depth value to the predetermined correction function; and correcting a fluorescence intensity by multiplying the depth correction factor.

In addition, the disclosure provides a method for correcting fluorescence data measurements, comprising: defining a border between a first layer and a second layer of a subject structure; calculating a depth of the second layer; calculating a depth calibration factor by plugging in a depth value to the predetermined correction table; and correcting a fluorescence intensity by multiplying the depth correction factor.

In yet additional embodiment, the subject method further comprises acquiring the fluorescence data and a structural data simultaneously.

In additional embodiments, the method further corrects the fluorescence data based on the distance between an optical probe and the structure prior to correcting the fluorescence data with depth calibration factor.

It is further contemplated that the method teaches the correction function being a function of depth of the fluorescence layer and an optical attenuation property of the first layer.

In yet additional embodiment, the method includes the border of the first and the second layer being defined by an automated algorithm. As well as, the border of the first and the second layer being provided by user input.

In further embodiments, the method teaches further displaying the corrected fluorescence data, wherein the fluorescence signal includes a near-infrared light, and/or is endogeneous fluorescence.

In further embodiments of the method, the fluorescence signal is emitted by an exogenous fluorescence agent.

Furthermore, the structural data and fluorescence data are both acquired using a single catheter. In addition, the structural data may be delivered by a core of a double clad fiber and the fluorescence data may be delivered by a cladding of the double clad fiber.

BRIEF DESCRIPTION OF THE DRAWINGS

FIG. 10c depicts the OCT images, all according to one or more embodiment of the subject apparatus, method or system.

FIGS. 11a-11d illustrate phantoms and a method of imaging the phantoms, according to one of the embodiments of the present disclosure.

FIGS. 12a-12d illustrate phantoms and a method of imaging the phantoms, according to one of the embodiments of the present disclosure.

FIG. 13a illustrates data acquired in imaging of phantoms shown in FIGS. 12a-12d, according to one of the embodiments of the present disclosure. Wherein FIG. 13b illustrating data generated by correcting the data shown in FIG. 13a, FIG. 13c illustrating correction curves generated from the data shown in FIG. 13b, and FIG. 13d illustrating a cross-section of the phantom shown in FIG. 12a.

FIG. 16 is a chart illustrating options of distance correction and how the distance correction and the depth correction are performed in each situation.

DETAILED DESCRIPTION

The following description is of certain illustrative embodiments, although other embodiments may include alternatives, equivalents, and modifications. Additionally, the illustrative embodiments may include several novel features, and a particular feature may not be essential to practice the devices, systems, and methods described herein.

Figure 1:
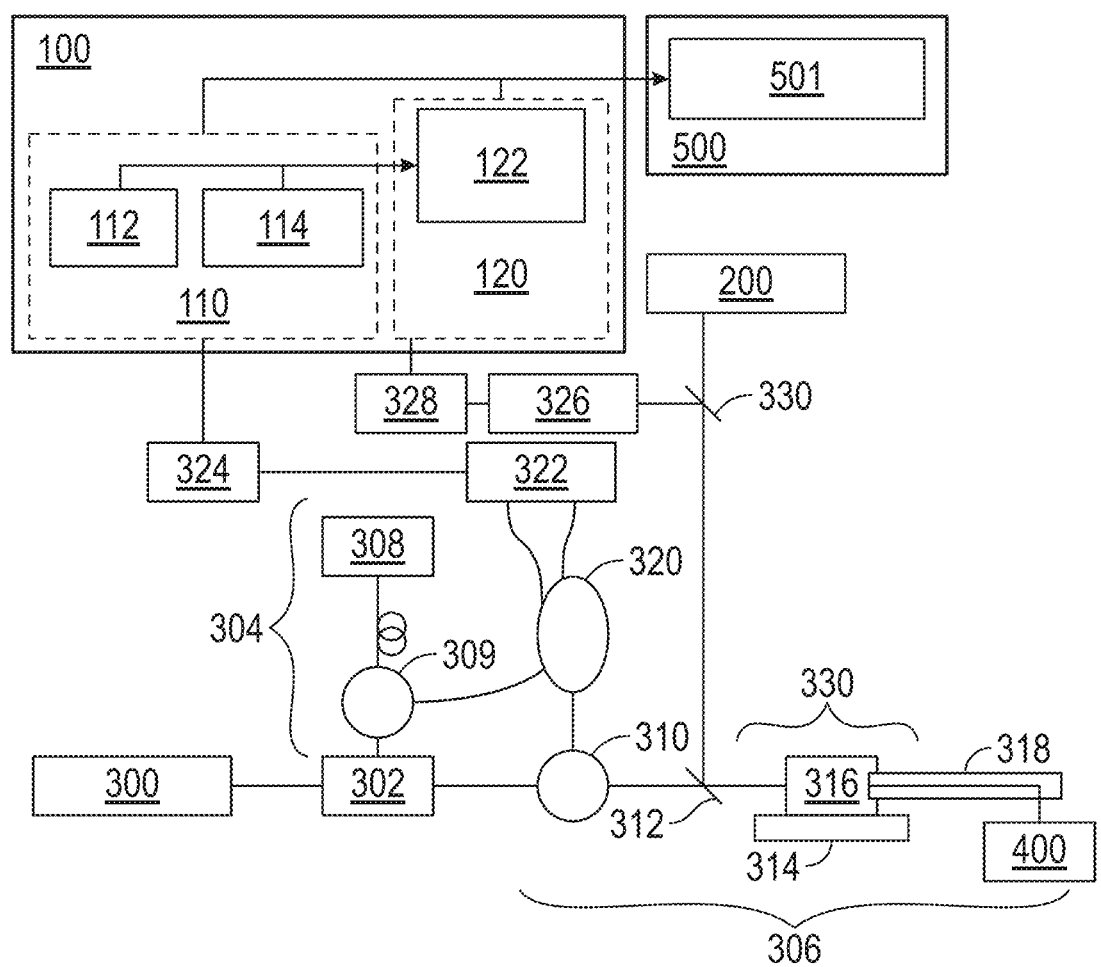
FIG. 1 is a schematic drawing of an OCT-fluorescence imaging system, according to one or more embodiment of the subject disclosure.

FIG. 1 is a schematic drawing of an OCT-fluorescence imaging system in one embodiment that can be applied as an intravascular OCT-fluorescence system for imaging of coronary arteries or other bodily lumens. The system may also be adapted to be used for esophageal imaging. An OCT light source 300 provides OCT light with a wavelength of around 1.3 µm is delivered and split into a reference arm 304 and a sample arm 306 with a splitter 302. A reference beam from the OCT light traveling along the reference arm 304 is reflected from a reference mirror 308 while a sample beam from the OCT light traveling along the sample arm 306 is incident and reflected or scattered from a sample 400 through a circulator 310, a rotary junction (RJ) 316, and a catheter 318. The sample arm 306 includes a patient interface unit (PIU) 330, and a catheter 318. The catheter 318 includes a double clad fiber (DCF) with a polished ball lens at the tip thereof for side-view imaging. The distal optics may alternatively include a DCF, a GRIN lens, and a refractive element (grating). PIU 330 includes a RJ 316 and pullback unit 314. In the OCT-fluorescence imaging system as shown in FIG. 1, excitation light provided by the excitation light source 200 is also directed to the rotary junction 316 and the catheter 318 to illuminate the sample 400. The excitation light incident on the sample 400 causes the sample 400 to emit fluorescence light. In one embodiment, the fluorescence light generated by the sample 400 may include autofluorescence, that is, the endogenous fluorescence light generated without application of a dye or an agent. Alternatively, the fluorescence light generated by the sample 400 may include fluorescence light generated by exogenous fluorescence dye or agent in the sample. The OCT light is delivered through the core of the double clad fiber, while the fluorescence light emitted from the sample 400 is collected by the cladding of the double clad fiber.

The system includes a coupler 320 in which the OCT light from the OCT light source 300 and the OCT light reflected from the sample 400 are coupled to generate interference patterns. The interference patters detected by a detector 322 such as a photodiode or multi-array camera and delivered to a processor such as a computer 100 through a data acquisition device 324. Simultaneously, the fluorescence light from the sample 400 is detected by a detector 326. The detector 326 records the fluorescence signal of the fluorescence light and delivers the fluorescence signal to the computer 100 via the data acquisition device 328. Preferably, the OCT interference patterns of the OCT lights and the fluorescence signal are delivered to the computer 100 simultaneously.

As shown in FIG. 1, the computer includes an OCT unit 110 for collecting and processing OCT data and a fluorescence unit 120 for collecting and processing fluorescence data. The OCT unit 100 includes a unit 112 for optical attenuation property calculation and a unit 114 for calculation of distance between the sample 400 and the exit end of the catheter 318 from which the OCT light is incident on the sample 400. The optical attenuation property and the distance calculated by the OCT unit 110 are output to the fluorescence unit 120. Based on the calculated optical attenuation property and the calculated distance, calibration of the fluorescence intensity is performed. Outputs of the OCT unit 110 and the fluorescence unit 112 are connected to the display 500 such that the OCT image and the calibrated fluorescence data can be displayed as a co-registered OCT-fluorescence image 501. In one embodiment, the information that correlates with the fluorescence collection efficiency other than optical attenuation property of the object is used instead of the distance between optical probe and the object. The information may correlate with the distance between optical probe and the object. For example, the intensity of the light reflected from the object may be used to calibrate the fluorescence.

As shown in FIG. 1, the position of the optical waveguide inside the catheter 318 can be adjusted or controlled by a pullback unit 314. In one embodiment, the rotary junction 316 is located on the pullback unit 314. The system further includes dichroic filters 312 and 330 for directing the OCT light and the fluorescence light to the desired locations/devices. The rotary junction rotates the optical probe inside the catheter 318 to obtain the cross-sectional images of the bodily lumens. The optical probe is simultaneously moved longitudinally during the rotation so that images are obtained in a helical scanning pattern. The rotation and translation movements of the OCT catheter scans the optical probe helically inside the bodily lumen, and produces a series of adjacent helical A-scans of the sample which can then be used to create a helical two-dimensional (2D) tomogram. Moving the catheter longitudinally within the bodily lumen allows the collection of a series of B-scans which can be combined to form a three-dimensional (3D) image of the sample of interest.

Figure 2:
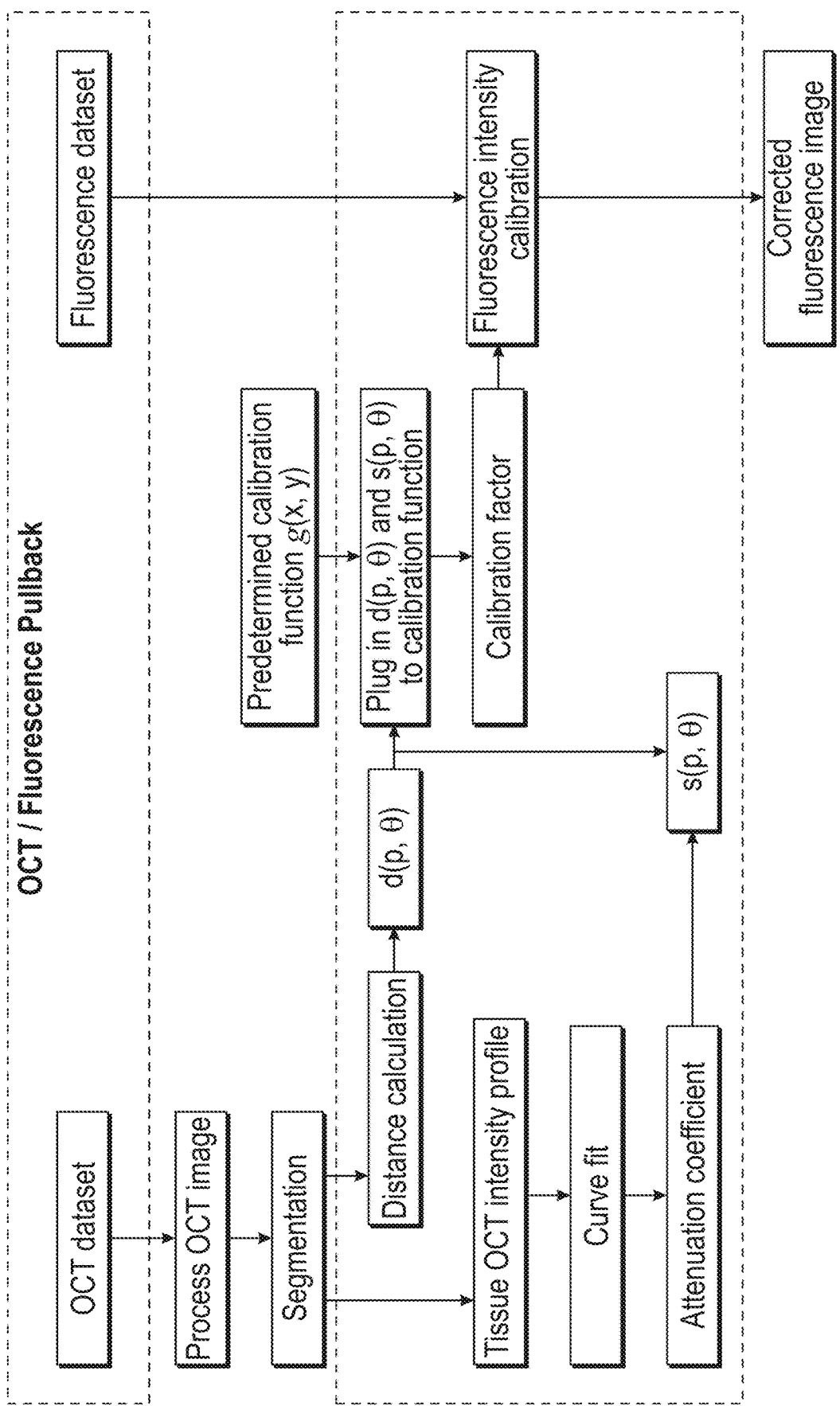
FIG. 2 is a flowchart of signal processing for an OCT-fluorescence imaging system, according to one or more embodiment of the subject disclosure.

FIG. 2 shows an exemplary flowchart for processing OCT-fluorescence image obtained from the sample. As discussed above, the OCT dataset and the fluorescence dataset are acquired simultaneously using a single catheter and delivered to the OCT unit and the fluorescence unit, respectively. In the OCT unit, the OCT image is constructed based on the OCT dataset. Preferably, the sample surface is automatically segmented through all OCT images at once. The distance between the catheter and the sample at the pullback position p and the angle $\theta$ is calculated from the segmented OCT image and stored as d(p, $\theta$). The OCT image includes of A-lines. The sample OCT intensity profile at the corresponding pullback position p and angle $\theta$ is extracted from the A-line at the position of p and the angle $\theta$. The optical attenuation properties s(p, $\theta$) is calculated by using the slope of the A-lines. By plugging d(p, $\theta$) and s(p, $\theta$) to the predetermined calibration function g(x, y), a fluorescence calibration factor is determined. The fluorescence dataset is processed for fluorescence intensity calibration by multiplying calibration factor. By applying this process to the entire OCT dataset from the pullback positions, entire fluorescence signal is corrected and the corrected fluorescence image can be obtained.

In one embodiment, a predetermined calibration factor table for variable distance and attenuation coefficient can be used instead of the predetermined calibration function. The distance d(p, $\theta$) and the optical attenuation property s(p, $\theta$) are calculated from the OCT image and the calibration factor for the closest d(p, $\theta$) and s(p, $\theta$) values are looked up from the calibration factor table. By multiplying the selected calibration factor to the fluorescence signal, fluorescence calibration can be performed.

Figure 3A:
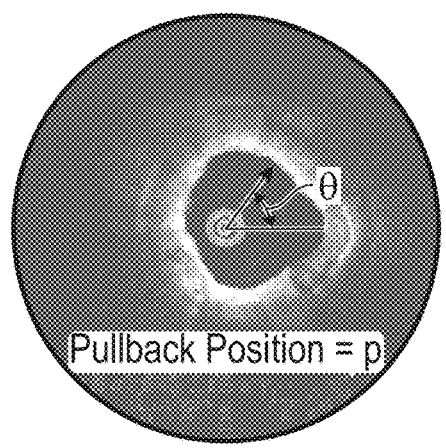
FIG. 3A-3B show exemplary OCT images of a coronary artery and the tissue intensity profile processed from an OCT imaging system, according to one or more embodiment of the subject disclosure.
Figure 3B:
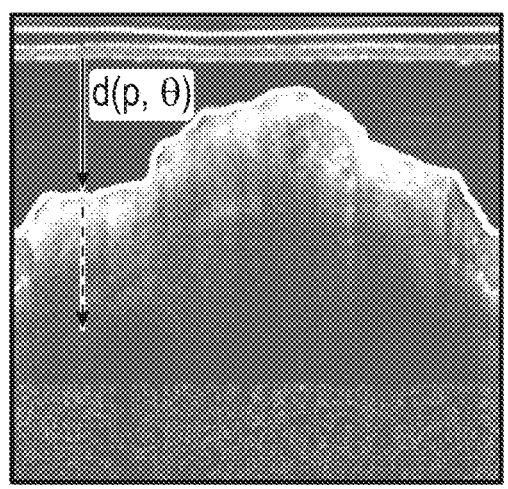
Figure 3C:
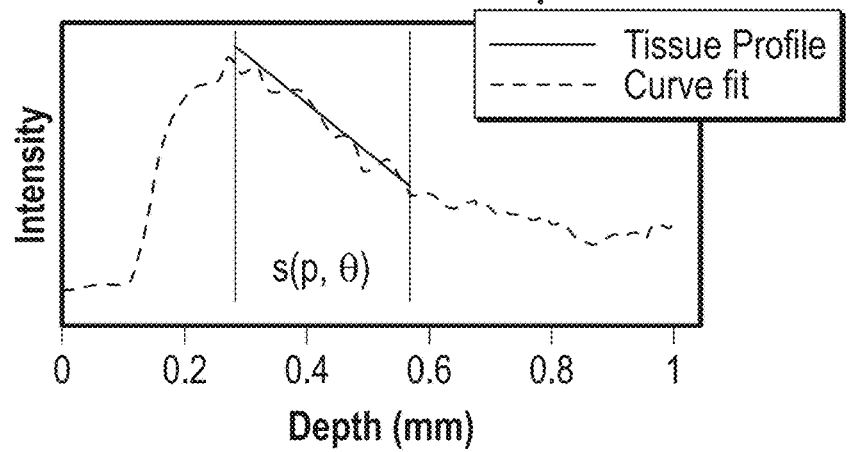
FIG. 3C is a graph showing tissue intensity profile at pullback, according to one or more embodiment of the subject disclosure.

FIG. 3A-3C shows an exemplary OCT image of a coronary artery and the tissue intensity profile processed from an OCT imaging system. In FIG. 3A, a cross sectional image of the coronary artery from an arbitrary pullback position p with reference to a polar coordination is presented. The segmentation of the OCT image is performed with the polar coordination image as shown in FIG. 3B. In FIG. 3B, the distance between the tissue and the catheter is shown by the solid arrow. The corresponding tissue region for optical attenuation property calculation is shown by the dotted arrow. The distance $d(p, \theta)$ between the catheter and the tissue lumen is calculated by a function of the pullback position p and angle $\theta$ as $d(p, \theta)$. The polar domain OCT image shows the segmented tissue lumen, the distance $d(p, \theta)$, and the corresponding tissue region used for calculating the optical attenuation property. Automatic segmentation and distance calculation algorithm can be used for distance calculation. The attenuation property $s(p, \theta)$ of the corresponding tissue region is calculated by analyzing the OCT intensity profile as shown in FIG. 3C.

As discussed above, the optical attenuation property of the fluorescence object is calculated using OCT intensity profile, that is, A-line. A total attenuation coefficient $\mu t$ is the summation of an absorption coefficient, $\mu a$, and a scattering coefficient, $\mu s$. Because the absorption coefficient $\mu a$ is much smaller than the scattering coefficient $\mu s$ at the wavelength of the OCT light, for example, 1.3 µm, the total attenuation coefficient $\mu t$ is approximately the same as the scattering coefficient as, that is, $\mu t \approx \mu s$. The attenuation coefficient can be extracted by fitting the compounded OCT A-line into a single scattering model, which is based on Beer-Lambert law, and accounts for the confocal point spread function property of sample arm optics. For example, fitting may be carried out by using least square fitting with the logcompressed A-line data. The maximum intensity point close to the lumen boundary may be used at the starting point for the line fitting. Adjacent A-line data may be averaged to reduce the noise.

Figure 4A:
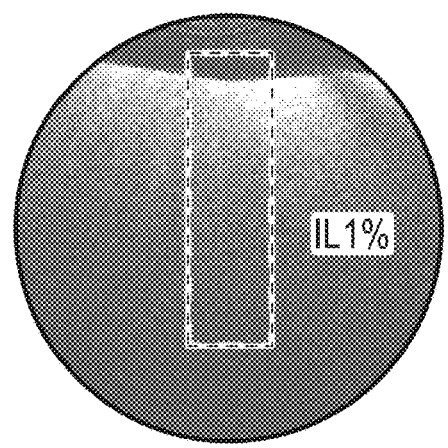
FIGS. 4A-4B show representative OCT images and A-line profile, according to one or more embodiment of the subject disclosure.
Figure 4B:
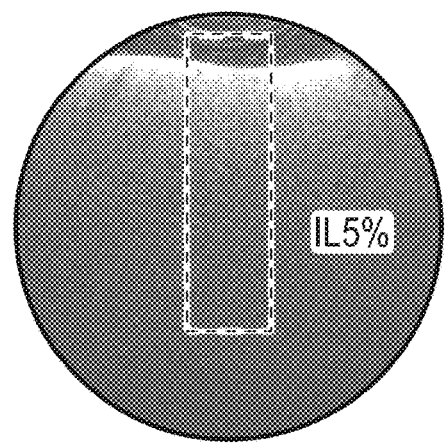
Figure 4C:
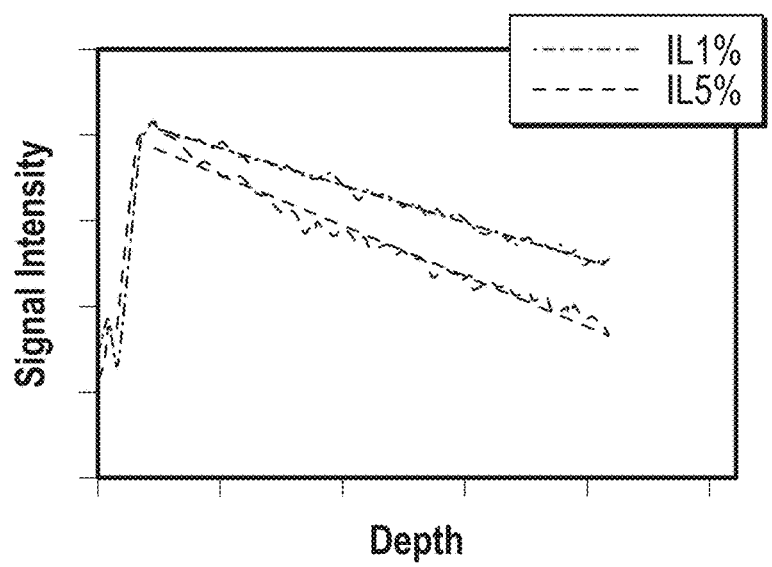
FIG. 4C is a graph depicting signal intensity against depth, according to one or more embodiment of the subject disclosure.

FIGS. 4A and 4B show the representative OCT images of fluorescence phantoms containing 1% and 5% intralipid, respectively. FIG. 4C shows averaged A-line profile of the phantoms (dotted lines) and the corresponding linear least square fit result (solid lines). The dotted rectangles in FIGS. 4A and 4B indicate the ROI for analysis. ROI is determined and the A-lines in the ROI are obtained. The boundary of the surface of the fluorescence object for each A-line is identified and averaged A-lines in the ROI are obtained. The linear least square fit is performed to the log-compressed averaged A-line and the slope value is used as the attenuation coefficient value.

The calibration function can be predetermined by measuring fluorescence intensity of phantoms with different optical properties as a function of distance between the optical probe (catheter) and the fluorescence object. To obtain the phantoms with various optical attenuation properties, phantoms containing scattering particles such as intralipid can be prepared and used. The attenuation coefficient of the phantoms can be measured by imaging phantoms with OCT and calculating the attenuation coefficient as described. Using multiple fluorescent phantoms with different optical properties, the fluorescence intensity profile as a function of distance for each optical property can be obtained. Based on the measurement, fitting model $f(x, y)$ as a function of distance (x) and attenuation coefficient (y) can be obtained. The calibration function for fluorescence intensity can be obtained as $g(x, y)=1/f(x, y)$. The calibration of the fluorescence signal is achieved by multiplying the calibration factor that is obtained by plugging in the distance (x) and attenuation coefficient (y) that corresponds to the each element of the fluorescence dataset.

The calibration function $f(x, y)$ can also be prepared as the set of the calibration function of distance (x) for representative attenuation coefficient values which the fluorescence object may show. Based on the measurement, fitting model $f(x)$ as a function of distance (x) for different optical properties can be obtained. The calibration function for the fluorescence intensity is obtained as $g(x)=1/f(x)$. The calibration function $g(x, y)$ can be obtained by selecting the calibration function closest to the sample attenuation coefficient value.

In one of the embodiments of the present disclosure, to each of the curves obtained from different phantoms an exponential model $f(x)=a*exp(b*x)+c*exp(d*x)$ can be applied for fitting. The constants (a) through (d) are determined in the fitting process. Also, each of the phantoms has a known attenuation property. Based on the known attenuation properties associated with the known curves, the computer 100 can determine a curve for a tissue which has a specific attenuation property by interpolation or extrapolation. In this embodiment, curve measurement are performed for multiple phantoms having specific attenuation properties (A1, A2, . . . An; $Ai \le Ai+1$, $1 \le i \le n$), curve fitting are performed for each measured curves and curve parameters are obtained (C1, C2, . . . , Cn; Ci=(ai, bi, ci, di), $1 \le i \le n$). These pieces of data are stored in a memory of the computer 100. In a case where tissue imaging is performed in-vivo, the system calculates the attenuation property Ax of the tissue. The computer 100 then selects known neighboring attenuation properties Aj, Aj+1 (Aj<Ax<Aj+1) and corresponding curve parameters Cj, Cj+1. By interpolation, the computer 100 can obtain a set of curve parameters Cx=(ax, bx, cx, dx), and by using the curve parameters and the exponential model, the computer 100 can perform distance correction.

FIGS. 11a-11d illustrates how multiple calibration curves $f(x)$ may be obtained. In FIG. 11A, a catheter 1101 is positioned in a cylindrical-shape phantom 1104a. The catheter 1101, can be the catheter 318 as illustrated in FIG. 1, is pulled back in a direction 1102 and may rotates in a direction 1103 during the entire pullback period. An axis l is set in a longitudinal direction of the catheter 1101, which is along the direction 1102. An axis d1 is perpendicular to the axis l, and is the radial direction of the rotation direction 1102.

The phantom 1104a has an inner region of which the cross-section is substantially circular and the diameter of the circle is greater along the l axis. The phantom 1104a is made of a material having a specific attenuation property Aa, and emits fluorescence light in response to excitation light emitted from the tip of the catheter. In FIGS. 11b-11d the configuration is the same as that illustrated in FIG. 11a, but the phantoms are made of different materials having different attenuation properties (Ab in FIG. 11b, Ac in FIG. 11c, and Ad in FIG. 11d). While the imaging is performed, the inner region of the phantom is filled with contrast agent, which is the same contrast agent to be injected into a human vessel to be imaged by the OCT-fluorescence imaging system. By performing OCT and fluorescence imaging of the phantoms in FIGS. 11a to 11d with the catheter during pullback and rotation, a set of OCT data and a set of fluorescence data are obtained. By analyzing the data, the computer 100 obtains the graphs in FIG. 4, and FIGS. 6a to 6d. The distance from the tip of the catheter 1101 to the surface of the phantom 1104A can be obtained from the OCT data.

The imaging of the phantoms 1104a to 1104d and the following correction data acquisition processes including curve fitting processes may be done in a factory. In this case the catheter or the rest of the OCT-fluorescence imaging system is not the one that is used for the actual in-vivo imaging in the hospital. One catheter of a specific type or one OCT-fluorescence imaging system of a specific type is used to determine the correction data acquisition processes, the data is stored in a memory of a computer 100 of the OCT-fluorescence imaging system of the same specific type, to be sold to a customer.

In another embodiment, the correction data acquired in the factory is stored in a separate computer readable medium bundled with a OCT-fluorescence imaging system of the same specific type, to be sold to a customer. In yet another embodiment, the correction data acquired in a factory is associated with a specific type of a catheter and/or specific type of a OCT-fluorescence imaging system, and stored in a server accessible by customers. In this case the computer 100 at customer's site obtains the correction data from the server, by sending information of the specific type of the catheter or the OCT-fluorescence imaging system. Alternatively, correction data may be in a computer readable medium.

In in-vivo imaging, fluorescence layers in a blood vessel have a relatively higher attenuation property, whereas non-fluorescence layers in a blood vessel have a relatively lower attenuation property. But for the artificially manufactured phantoms, it is possible that a phantom made of fluorescence material having a lower attenuation property is manufactured. The distance correction function is dependent on the attenuation property of the first layer (from the inner surface) of the vessel, and it does not matter if the first layer is a fluorescence layer or a non-fluorescence layer. Therefore, the set of calibration curves obtained from imaging of the phantoms 1104a to 1104d can be used for the distance correction, in a situation that the first layer is a non-fluorescence layer and the second layer below the first layer is a fluorescence layer. This will be described in greater detail with reference to FIGS. 7 to 16.

Figure 5:
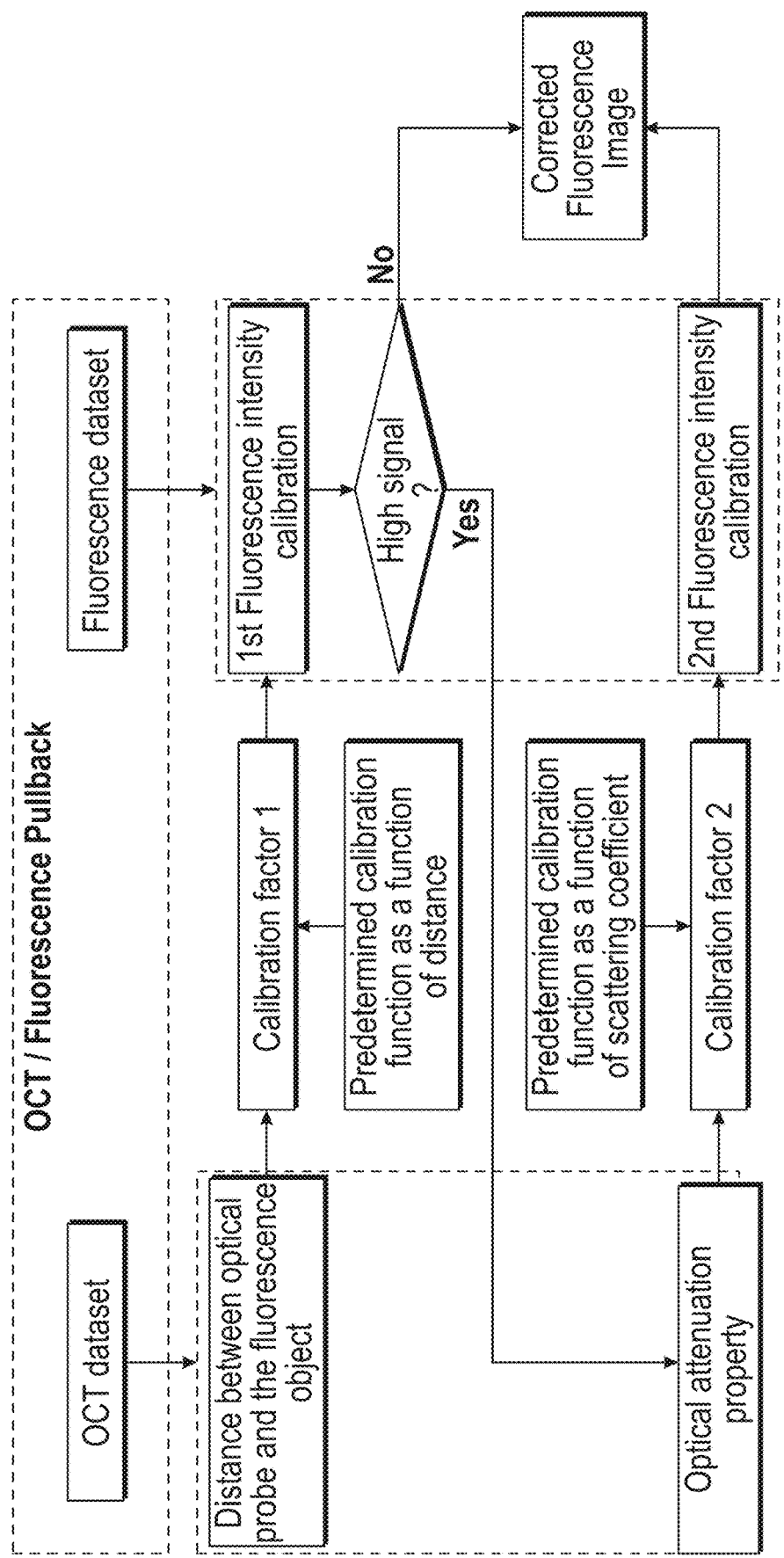
FIG. 5 is a flow chart of signal processing algorithm for an OCT-fluorescence imaging system, according to one or more embodiment of the subject disclosure.
Figure 6A:
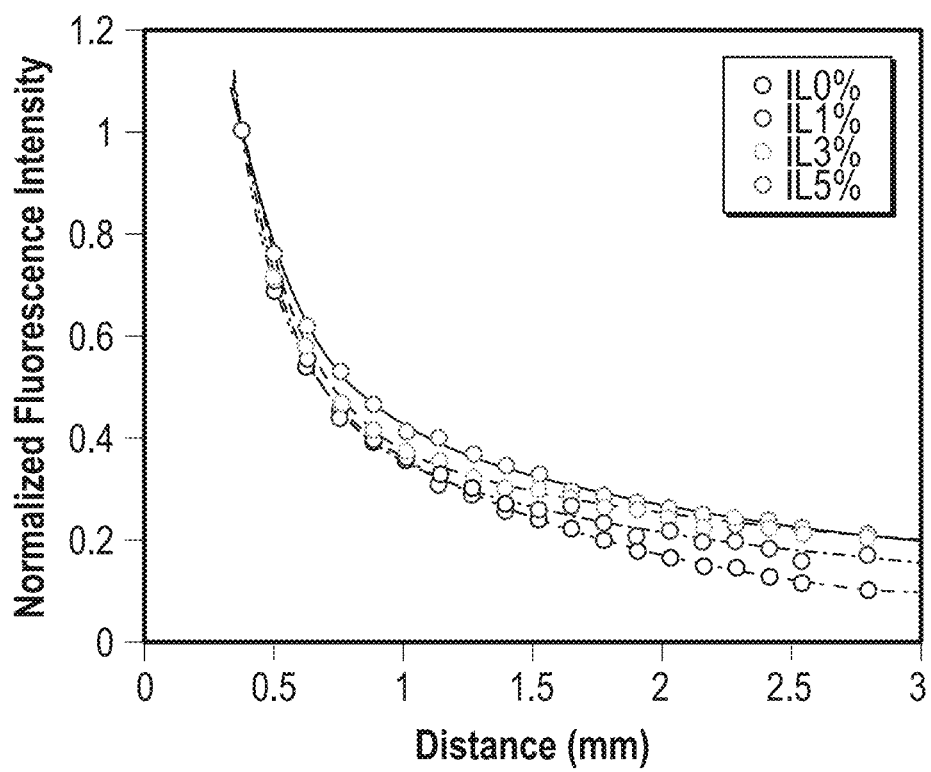
FIGS. 6A-6D are graphs providing various examples of fluorescence calibration, according to one or more embodiment of the subject disclosure.
Figure 6B:
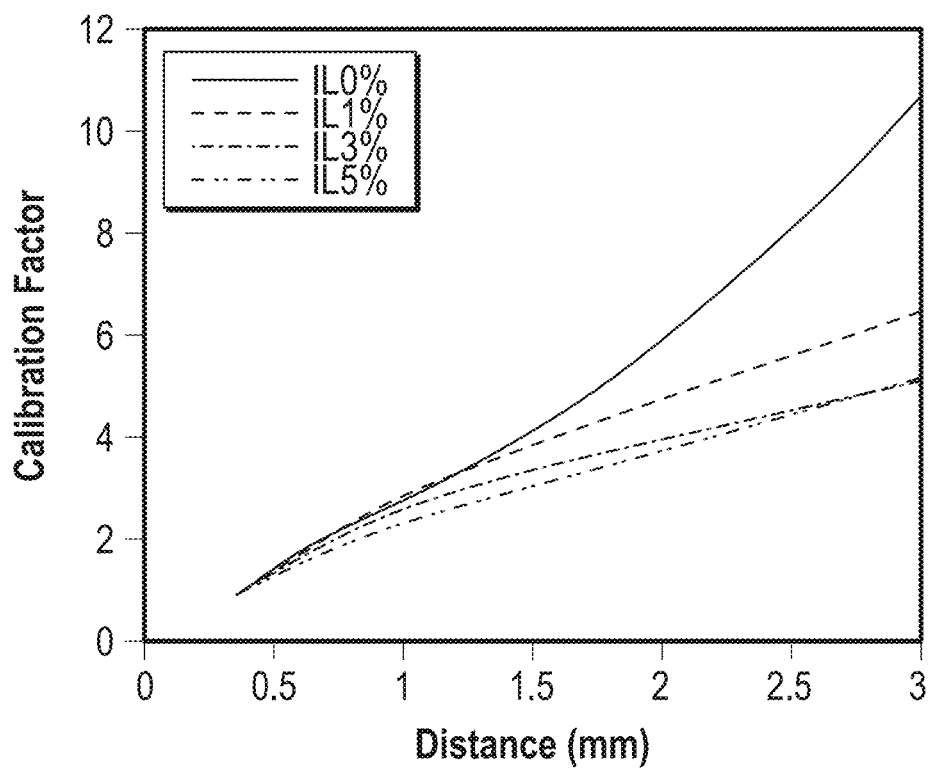
Figure 6C:
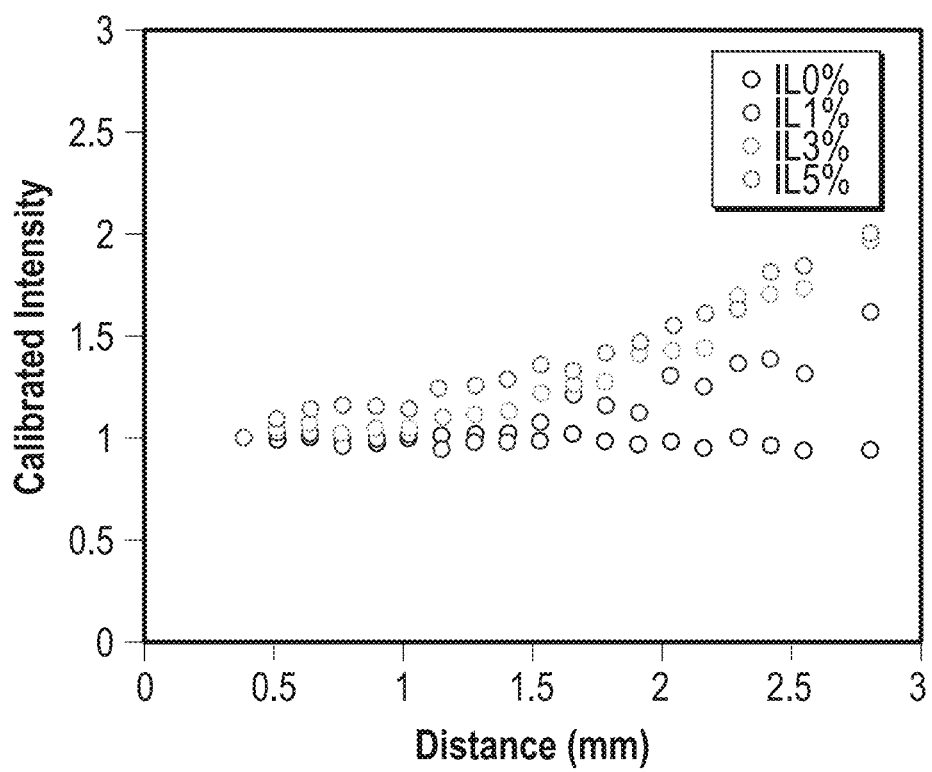
Figure 6D:
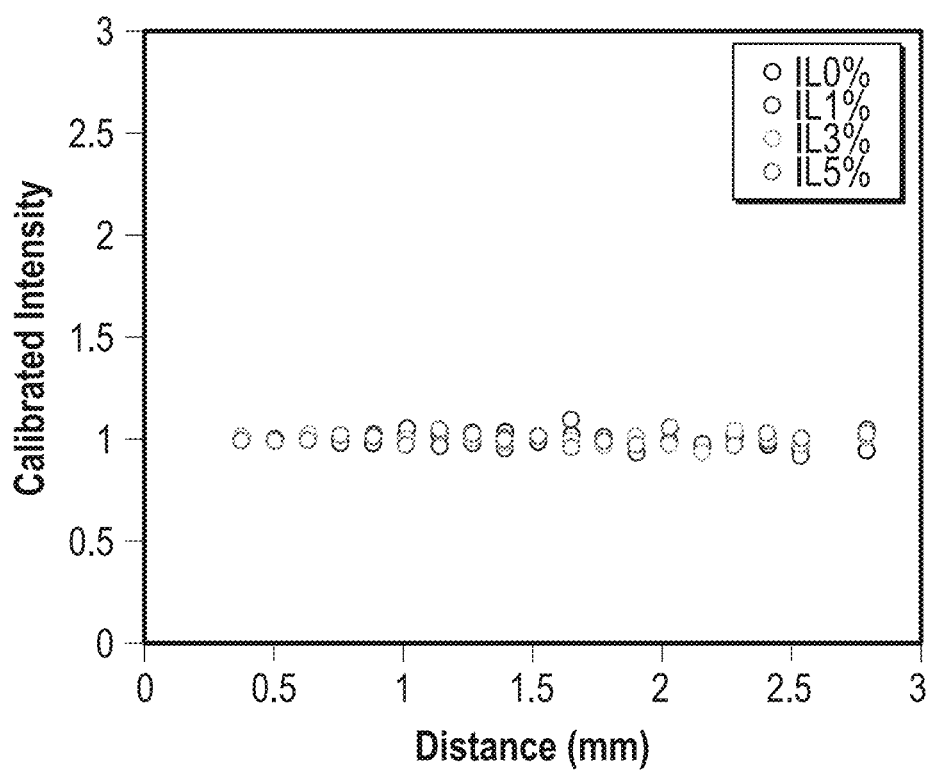

FIG. 5 shows the flowchart of signal processing of the OCT-fluorescence image in another embodiment. Preferably, the OCT dataset and the fluorescence dataset are simultaneously delivered to the processing unit. In the OCT unit, the distance between the catheter and the fluorescence object is calculated and plugged into a predetermined calibration function to obtain calibration factor 1. The calibration factor 1 is input to the fluorescence unit. A first fluorescence intensity calibration is performed by multiplying the calculated factor. If the corrected fluorescence intensity is high, for example, above a predetermined level, an optical attenuation property is calculated in the OCT unit. A calibration factor is obtained by plugging the calculated optical attenuation property in a predetermined calibration function as a function of attenuation coefficient to obtain calibration factor 2. The fluorescence intensity is then calibrated by calibration factor 2. The corrected fluorescence image can thus be obtained based on the fluorescence intensity calibrated by calibration factor 1 and/or calibration factor 2.

FIG. 6 shows the exemplary result of the calibration method as shown in FIG. 5. Fluorescence intensity of phantom containing different concentration of intralipid (0%, 1%, 3%, 5%) and Alexa Fluor 633 dye is measured using fiber optical probe having ball lens at the distal end. FIG. 6A shows the normalized fluorescence intensity as a function of distance between optical probe and fluorescence phantoms and the corresponding exponential fitting curve $f(x)$ through the data. From this data, calibration factor as $1/f(x)$ was calculated (FIG. 6B). FIG. 6C shows the calibrated fluorescence intensity using single calibration function for 0% intralipid (IL0%) and FIG. 6D shows the calibrated fluorescence intensity using calibration functions that corresponds to the attenuation coefficient of each phantoms. These results demonstrate that the calibration method that takes optical attenuation property into account (FIG. 6D) provides the accurate fluorescence intensity calibration.

In above described embodiments, the method of determining a distance correction curve based on the attenuation property of the tissue of the vessel emitting fluorescence. These methods can be applied to the vessel having a fluorescence layer (tissue) on the surface of the vessel. But there are some situations in which fluorescence layer is not at the surface of the vessel, and non-fluorescence layer is on top of the fluorescence layer. In this situation, depth of the non-fluorescence layer on top of the fluorescence layer is considered and distance correction (or depth correction) is performed for the non-fluorescence layer. These methods according to embodiments of the present disclosure are described below.

Figure 7:
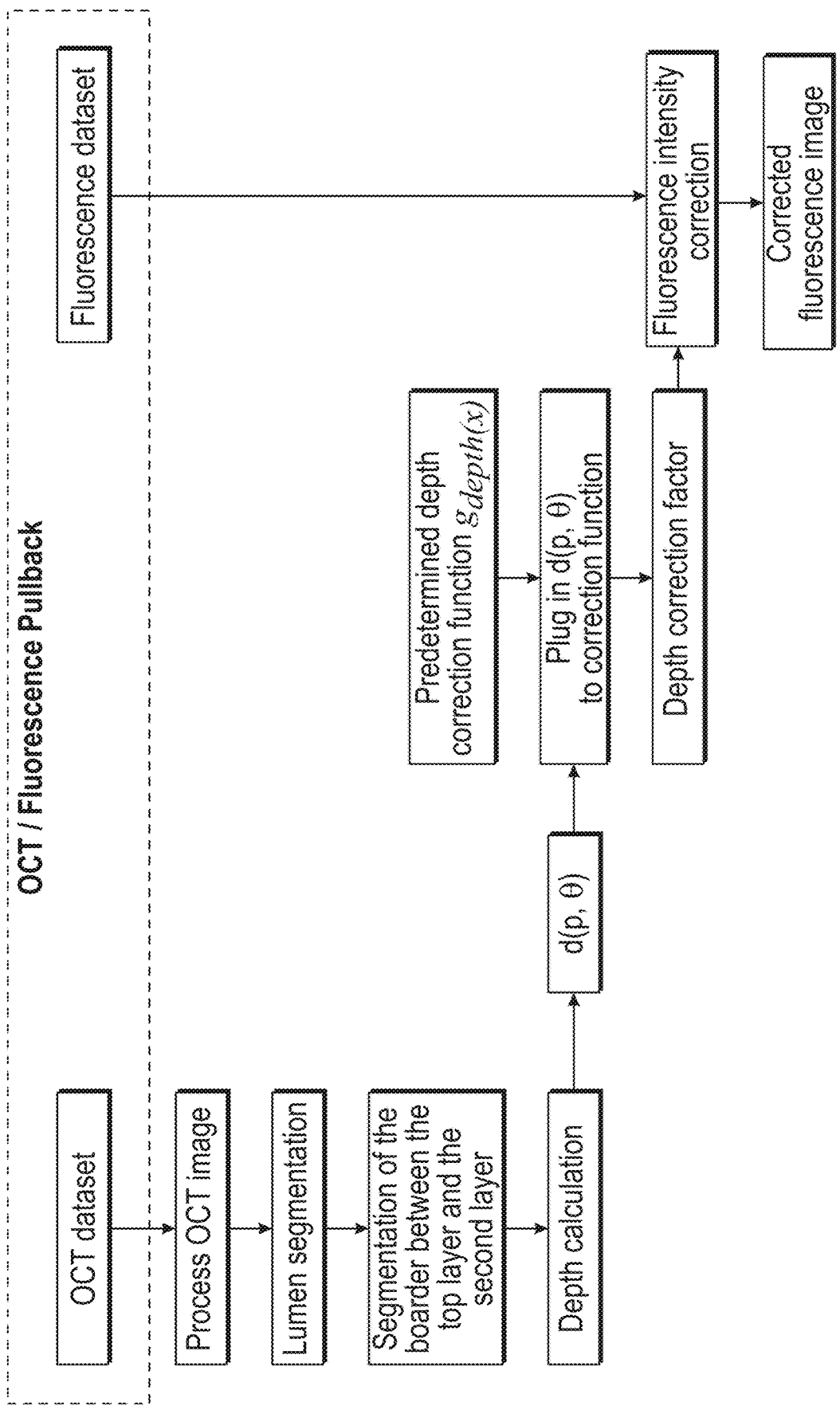
FIG. 7 provides a flowchart of the signal processing algorithm, according to one or more embodiment of the subject apparatus, method or system.

FIG. 7 shows the exemplary flowchart of the present method. The OCT dataset and fluorescence dataset are acquired simultaneously using a single catheter. The OCT image is constructed from the OCT dataset and segmented to define the lumen. The OCT image is further segmented to define the border between the top layer and the second fluorescence layer. The depth of the second layer from the lumen at pullback position p and the angle θ is calculated from the border and lumen values as d(p, θ). The depth-correction factor is obtained by plugging in d(p, θ) to the predetermined depth correction function $g_{depth}(x)$. Then the corrected fluorescence intensity is obtained by multiplying the correction factor to the fluorescence value at the corresponding pullback position and the angle. In FIG. 7, only the depth correction for the first non-fluorescence layer on top of the second fluorescence layer is performed, and the distance correction for the inner region of the vessel is not performed. This exemplary process may be applied to the situation in which OCT and fluorescence imagings are performed for a vessel with a small diameter which is almost the same as the diameter of the catheter 318. In this situation there is no or little distance between the catheter 318 and the vessel to be imaged, and distance correction can be skipped.

FIGS. 12a-d and 13 illustrates the method of obtaining the depth correction function $g_{depth}(x)$ is obtained. FIGS. 12a-12d illustrates situation as to how multiple calibration curves $f(x)$ are obtained. In FIG. 12d, a catheter 1201 is positioned in a cylindrical phantom having a material 1204a and a material 1205. The catheter 1201 can be the catheter 318 as illustrated in FIG. 1, is pulled back in a direction 1202 and rotates in a direction 1203 during an entire period of the pullback. An axis l is set in a longitudinal direction of the catheter 1201, which is along the direction 1202. An axis d1 is perpendicular to the axis d1, and is the radial direction of the rotation direction 1202.

The material 1204a of the phantom defines an inner region of which the cross-section is substantially circular, and the diameter of the circle is constant as D, along the l axis. The material 1204a is made of a material having a specific attenuation property Aa', and does not emit fluorescence light in response to excitation light emitted from the tip of the catheter 1201. In a plane perpendicular to the l axis, the material 1204a has a ring-shape cross-section with a width d2. The width d2 becomes monotonically larger along the l axis. The material 1205 does emit fluorescence light in response to excitation light emitted from the catheter 1201. In a plane perpendicular to the l axis, the material 1205 has a ring-shape cross-section surrounding the inner ring defined by the material 1204a. The width the ring defined by the material 1205 may be smaller along the l axis but the width and shape can be different as long as the material 1205 surrounds the material 1204a. The material 1204a and material 1205 are fixed with each other, so as to form one cylindrical phantom.

In FIGS. 12b-12d the configuration is the same as that illustrated in FIG. 12a, but the phantoms material 1204a is replaced with a material 1204b in FIG. 12b, and again replaced with a material 1204c in FIG. 12c, and finally replaced with a material 1204d in FIG. 12d. The materials 1204a to 1204d have different attenuation properties (Aa' for the material 1204a, Ab' for the material 1204b, Ac' for the material 1204c, and Ad' for the material 1204d). All of these materials are non-fluorescence material, which do not emit fluorescence light in response to the excitation light from the catheter 1201. In FIGS. 12b to 12d, the same material 1205 as the phantom in FIG. 12s is used for these cylindrical phantoms.

While the imaging is performed, the inner region of the phantom is filled with a contrast agent, which is the same contrast agent to be injected into a human vessel to be imaged by the OCT-fluorescence imaging system. By OCT and fluorescence imaging of these four cylindrical phantoms, the computer 100 obtains OCT data and fluorescence data.

Figure 13A:
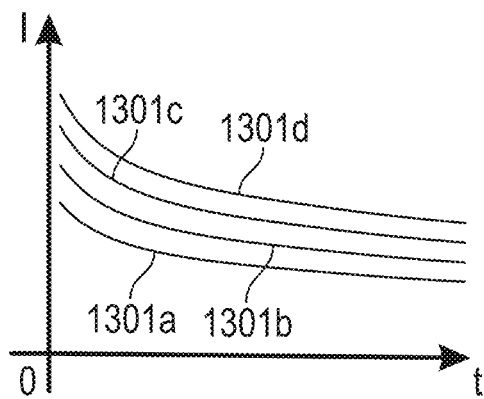
Figure 13B:
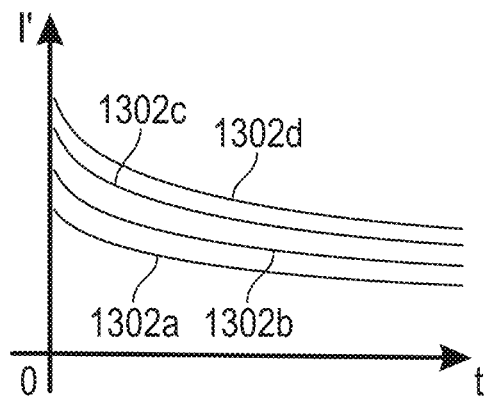
Figure 13C:
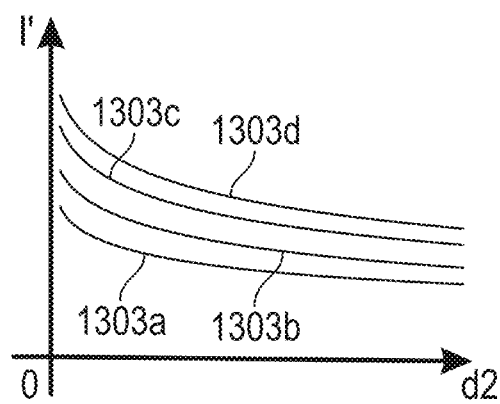

FIGS. 13a to 13c illustrates fluorescence data and how the data is converted into the correction data. FIG. 13a illustrates fluorescence data obtained with the catheter 1201 and the OCT-fluorescence system during the pullback. The horizontal axis represents time t of the data acquisition, and the vertical axis I represents the intensity of the fluorescence. The graphs 1301a, 1301b, 1301c, and 1301d correspond to the cylindrical phantoms in FIGS. 12a to 12d, respectively. Because the diameters of the materials 1204a to 1204d (d2) is larger along the l axis, the intensities become smaller along the t axis. Because the attenuation properties are different in different phantoms, the curves are different. In addition, graphs 1302a, 1302b, 1302c, and 1302d correspond with FIG. 13b, and 1303a, 1303b, 1303c, and 1303d correspond with FIG. 13c.

FIG. 13b illustrates fluorescence data corrected by the distance correction process. Even though the cylindrical phantoms in FIGS. 12a to 12d are designed so that the inner diameter D is constant, the actual diameters should be different from D and are also different in positions in the l axis, due to error manufacturing process of these phantoms. For a normalization purpose to remove the effect of the error, the distance correction is applied to the data. The distance correction can be performed by conventional methods, in which a single reference correction function is provided based on results of imaging of a phantom, and the reference correction data is used. The horizontal axis t is the same as that of FIG. 13a, but the vertical axis I' is different from that of FIG. 13a. I' can be obtained by multiplying (or dividing) the reference correction coefficient with the fluorescence data I. The reference correction coefficient is determined by the reference correction data and the distance from the center of the catheter 1201 and the surface of the material 1204a (1204b, 1204c or 1204d). The distance can be obtained from the OCT data. Here in this distance correction process, theoretically, the correction function can be dependent on the material 1204a, 1204b, 1204c or 1204d, but because the difference $\delta=d1-D$ (d1 is the actual distance from the center of the catheter 1201 and the surface of the material 1204a, 1204b, 1204c, or 1204d) is so small, there is practically no issue with using a single reference correction function.

Figure 13D:
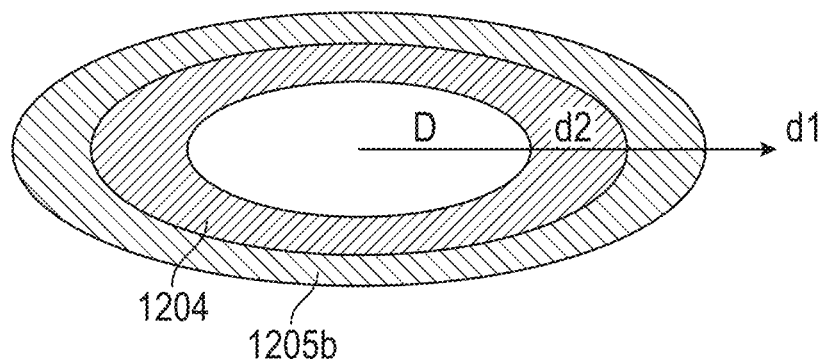

FIG. 13c illustrates correction curve $f_{depth}(x)$. The horizontal axis represents d2, which is the width of the material 1204a as shown in FIG. 13d. The vertical axis represents I', which is the same as that of FIG. 13b. The $f_{depth}(x)$ is obtained by curve fitting of the data shown in FIG. 13b. The fitting model can be $f(x)=a'*exp(b'*x)+c'*exp(d'*x)$. The correction function $g_{depth}(x)$ can be obtained as $1/f_{depth}(x)$. Each of the correction functions can be defined by a set of parameters $C'=\{a', b', c', d'\}$.

Now the four correction curves $f_{depth\_a}(x)$, $f_{depth\_b}(x)$, $f_{depth\_c}(x)$, $f_{depth\_d}(x)$, or the 4 correction functions $g_{depth\_a}(x)$, $g_{depth\_b}(x)$, $g_{depth\_c}(x)$, $g_{depth\_d}(x)$, are obtained through the above described processes. These correction functions $g_{depth\_a}(x)$, $g_{depth\_b}(x)$, $g_{depth\_c}(x)$, $g_{depth\_d}(x)$ are associated with attenuation properties Aa', Ab', Ac', and Ad', respectively. By applying interpolation or extrapolation methods, the computer 100 can obtain a specific correction function $g_{depth\_t}(x)$ for a specific tissue having an attenuation property At, if the At is close to or in a range of {Min(Aa', Ab', Ac', Ad'), Max(Aa', Ab', Ac', Ad')}. For example, if the attenuation property At meets the following condition, Ab'<At<Ac', the system performs interpolation using $g_{depth\_b}(x)$ and $g_{depth\_c}(x)$ (or, $f_{depth\_b}(x)$, $f_{depth\_c}(x)$) to obtain the correction function $g_{depth\_t}(x)$ for the specific tissue.

Figure 14:
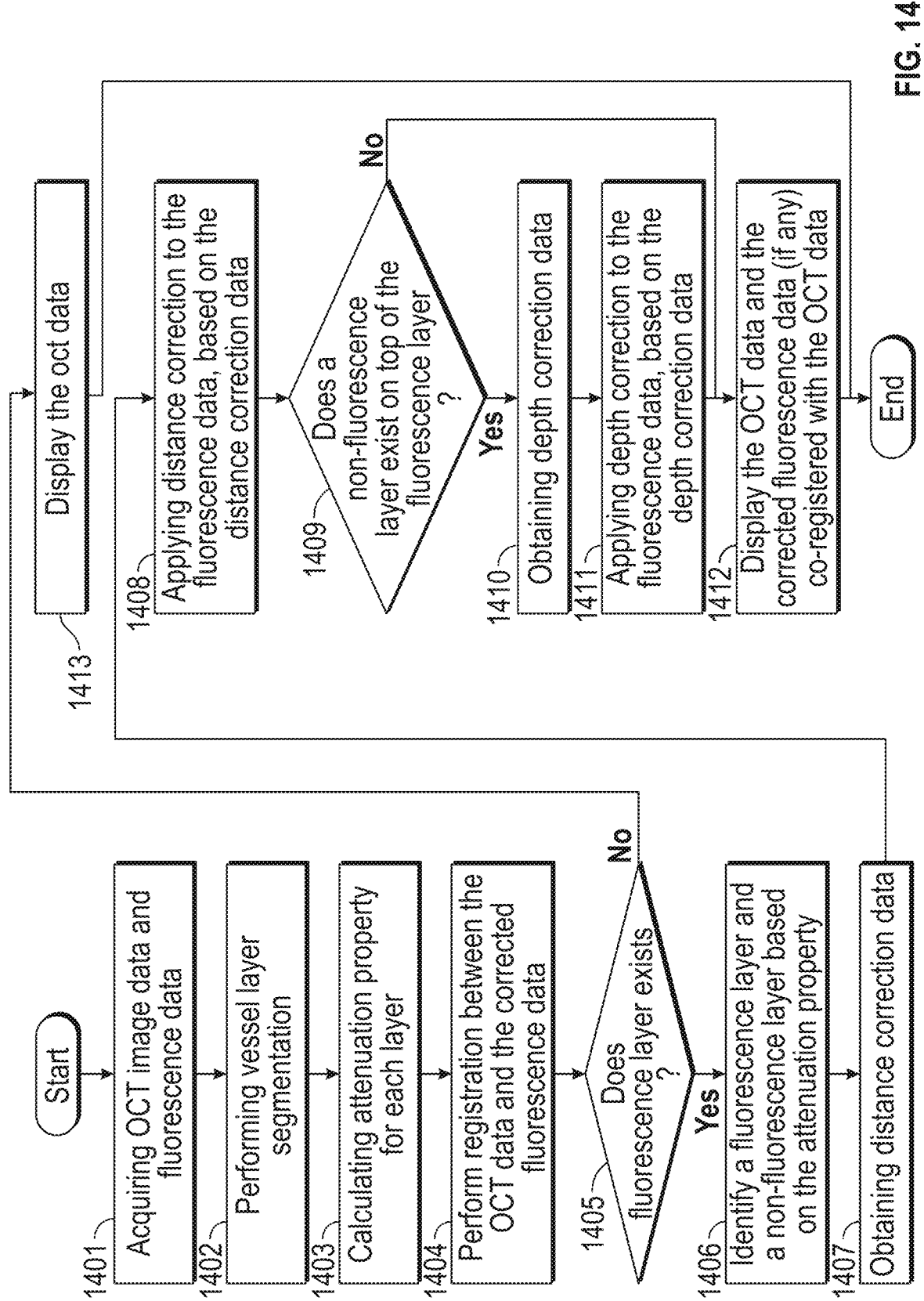
FIG. 14 shows a flowchart for correcting fluorescence data, according to one or more embodiment of the subject apparatus, method or system.

FIG. 14 shows a flowchart describing a process of correcting fluorescence data using the correction functions obtained in one of the methods detailed above, according to one of the embodiments of the present disclosure. In step S1401, the OCT-fluorescence imaging system performs OCT imaging and fluorescence imaging of a vessel in-vivo, to acquire OCT image data and fluorescence data. In step S1402, the computer (or the OCT unit in the computer) performs segmentation of the vessel region to determine one or more layers in the region. The segmentation is performed by analyzing intensities of the OCT image. In this process one or more layers in the vessel are segmented. In step S1403, the computer performs registration between the OCT image data and the fluorescence data. In the registration process, time stamp data associated with each A-scan data of the OCT image data and each piece of the fluorescence data is used to determine which A-scan data and which piece of the fluorescence data are acquired at the same time. In step S1404, the computer calculates attenuation property for each layer segmented in the step S1402.

In step S1405 of FIG. 14, the computer determines if a fluorescence layer in the imaged vessel. This determination can be made based on the attenuation property calculated for the segmented layer. If the attenuation property is equal to or larger than a certain threshold, the computer determines that the layer can emit fluorescence in response to excitation light from the catheter. If the attenuation property is smaller than a certain threshold, the computer determines that the layer is a non-fluorescence layer, which cannot emit fluorescence in response to excitation light from the catheter. This criterion can be applied to in-vivo imaging of a blood vessel. By using this method, the computer obtains where in the imaged vessel in the longitudinal direction the fluorescence layer exists, and even if there are multiple layers stacked in a depth or radial direction, the computer obtains which of the multiple layers a fluorescence layer is. By using this method, the following steps S1406 can be performed in this step S1405 as shown above.

The determination can be made based on the fluorescence data. If there is no or little fluorescence intensity acquired by the catheter, the computer determines that the there is no fluorescence layer existed in the imaged vessel. If there is fluorescence data whose intensity is larger than a certain threshold, the computer determines that the fluorescence layer exists in the imaged vessel. By using this method, the computer also obtain where in the imaged vessel in the longitudinal direction the fluorescence layer exists, but if there are multiple layers stacked in a depth or radial direction, the computer cannot identify which of the multiple layers a fluorescence layer is. In other to identify which layer is a fluorescence layer, the computer applies a different method as shown above by using attenuation properties of the layers. But by this method of using fluorescence intensity instead of the calculated attenuation properties, the computer can easily determines if there is any fluorescence layer in the imaged vessel. In this case, step S1405 can be performed before step S1404, so that the computer can skip step S1404 and proceed to steps S1406 through S1409, which reduces processing time for imaging to displaying of the image.

In yet another embodiment, the computer utilizes both methods of (1) using the attenuation property and (2) using the fluorescence intensity. In one embodiment, the result of either (1) or (2) indicates that there is a fluorescence layer, the computer determines that the fluorescence layer exists. This method contributes to display as much fluorescence data as possible. In another embodiment, the results of both (1) and (2) indicate that there is a fluorescence layer in the imaged vessel, the computer determines that the fluorescence layer exists. This method contributes to improving liability of the fluorescence data displayed with the OCT image data.

If the computer determines that fluorescence layer exists, the process proceeds to S1406; if not, the process proceeds to S1413. In step S1413 the computer causes the display to display the OCT image data, without displaying fluorescence data, because it is determined that the fluorescence layer does not exist in the imaged vessel.

In step S1406, the computer identifies the segmented layer as a fluorescence layer or a non-fluorescence layer, based on the attenuation property.

Figure 15:
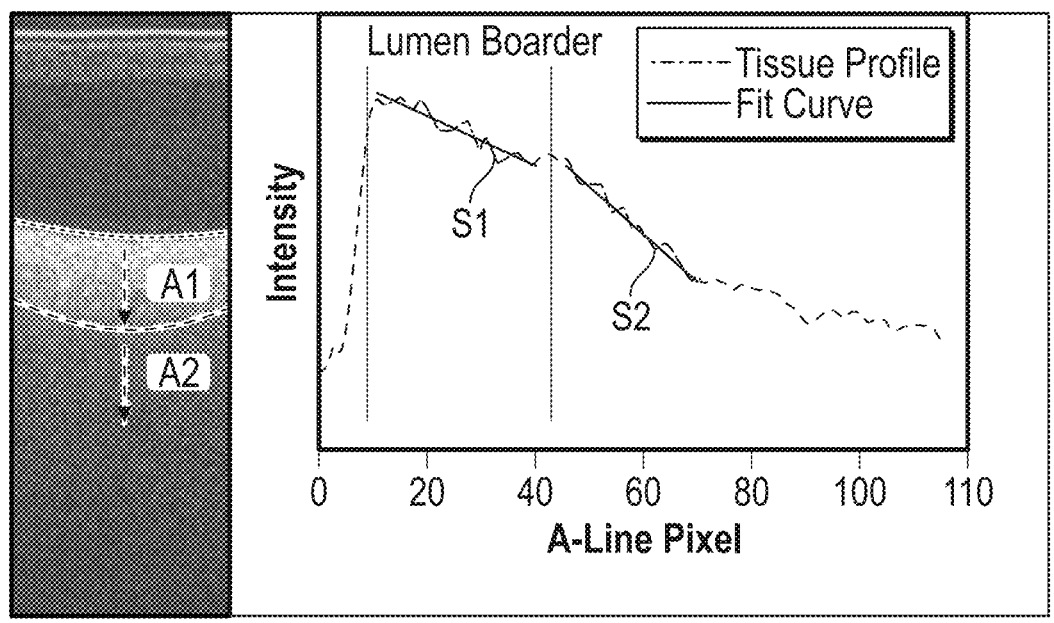
FIG. 15 illustrates an OCT image of a manufactured phantom, and a graph of intensity of an A-scan, according to one or more embodiment of the subject apparatus, method or system.

FIG. 15 illustrates an exemplary process of steps S1404 through S1406. The exemplary process describes a process of calculating attenuation properties of 2 layers, A1 and A2, in the vessel. A Polar domain image of OCT is shown on the left side. The polar domain image shows the lumen and the border between the top layer and the second fluorescence layer. The dotted arrow indicates the tissue region for scattering property calculation. On the right side, an OCT intensity profile corresponding to the dotted arrow in image A is shown. Segmentation of the lumen and the border between the top layer and the second fluorescence layer can be processed automatically by the software algorithm in the step S1402. At the frame of interest for correcting fluorescence, an edge detection algorithm can be performed to provide the coordinates of the lumen and the border between the top layer and the second fluorescence layer. The coordinates of the lumen and the border between the top layer and the second fluorescence layer can be further adjusted with user input. In another embodiment, the border between the top layer and the second fluorescence layer can be defined manually using user input to delineate the border contour.

The attenuation property of the first layer (S1) and the second layer (S2) are calculated using OCT intensity profiles. OCT intensity profiles can be obtained by averaging the adjacent A-line intensity profiles from the coordinates of the lumen (A1) and the border between the top layer and the second fluorescence layer (A2). The attenuation coefficient can be estimated by fitting the averaged OCT A-line intensity profiles into a single scattering model. The attenuation coefficient is estimated by least square fitting of the log-compressed averaged A-line intensity profiles with a linear model.

Depth correction can be applied to the second layer. In one embodiment, depth correction is applied only when the attenuation coefficient of the second layer is higher than the first layer, which implies advanced plaque tissue characteristics in the second layer such as necrotic core or macrophage infiltration.

In one variant, step S1406 can be performed after the steps S1407 and S1408 for distance correction.

In step S1407, the computer obtains distance correction data and can perform (1) a conventional distance correction method using a single correction function defined independently from the characteristics (attenuation property) of a top layer in the vessel; or (2) a distance correction method using a correction function dependent on the characteristics of a top layer in the vessel. The user can select which of the options (1) and (2) is applied to the fluorescence data. This will be described later with reference to FIG. 16.

Where the option (1) is applied, the computer obtains a distance correction function from its memory. In a case where the option (2) is applied, the computer obtains a distance correction function based on the g(x,y) as described with reference to FIGS. 1-6.

In step S1408, the computer applies distance correction to the fluorescence data based on the obtained distance correction function (data). In step S1409, the computer determines if a non-fluorescence layer exists on top of the fluorescence layer. This determination can be made based on the results of the step 1407. If it is determined that the non-fluorescence layer exists, the process proceeds to step S1410 to perform depth correction of the top layer. If it is determined that the non-fluorescence layer does not exists, the process proceeds to step S1412.

In step S1410, the computer obtains depth correction data $g_{depth\_t}(x)$ based on the attenuation property and the correction functions $g_{depth\_a}(x)$ through $g_{depth\_d}(x)$ which can be generated by the methods described with reference to FIGS. 12 and 13. In step S1411, the computer applies depth correction to the fluorescence data, based on the depth correction data.

In step S1412, the computer causes the display to display the OCT image data and the corrected fluorescence data which is registered with the OCT image data.

FIG. 16 is a chart illustrating options (1) and (2) and how the distance correction and the depth correction are performed in each situation. As described above, in response to a users selection, the computer determines which of the options (1) and (2) is applied to the fluorescence data. In option (1), the distance correction for the inner region of the vessel is performed based on a single correction function independent from the top layer of the vessel wall. In option (2), the distance correction for the inner region of the vessel is performed based on a correction function dependent on the top layer of the vessel wall.

In option (1), where there is a non-fluorescence layer on top of the fluorescence layer, the distance correction is performed by using the single function, and the depth correction is performed based on the correction function determined by the attenuation property of the top layer of the vessel wall.

In option (1), where there is a fluorescence layer on top, the distance correction is performed by using the single function, and the depth correction is not applied.

In option (1), where there are non-fluorescence layers only, the distance correction or the depth correction is not applied.

In option (1), where there is a fluorescence layer only, the distance correction is performed by using the single function, and the depth correction is not applied.

In option (1), where there is a non-fluorescence layer only, the distance correction or the depth correction is not applied.

In option (2), where there is a non-fluorescence layer on top of the fluorescence layer, the distance correction is performed based on the correction function determined by the attenuation property of the top layer of the vessel wall, and the depth correction is performed based on the correction function determined by the attenuation property of the top layer of the vessel wall.

In option (2), where there is a fluorescence layer on top, the distance correction is performed based on the correction function determined by the attenuation property of the top layer of the vessel wall, and the depth correction is not applied.

In option (2), where there are non-fluorescence layers only, the distance correction or the depth correction is not applied.

In option (2), where there is a fluorescence layer only, the distance correction is performed based on the correction function determined by the attenuation property of the top layer of the vessel wall, and the depth correction is not applied.

In option (2), where there is a non-fluorescence layer only, the distance correction or the depth correction is not applied.

The depth correction in one of the embodiments of the present disclosure is basically a distance correction for the top non-fluorescence layer of the vessel. In both depth correction and distance correction, the distance correction coefficient g(x) or the depth correction function $g_{depth}(x)$ is multiplied with the fluorescence intensity. Accordingly, the order of these corrections are interchangeable.

In another embodiment, a predetermined correction factor table for varying depth can be used instead of the predetermined correction function. In this case, the d(p, θ) is calculated from the OCT image and the correction factor for the closest d(p, θ) value is looked up from the correction factor table. By multiplying the selected calibration factor to the fluorescence value, fluorescence correction may be carried out.

The depth correction function can be predetermined by measuring fluorescence intensity of phantoms with a varying depth of fluorescence layer from the surface. To obtain the phantoms with varying depth, phantoms containing scattering particles, such as intralipid or TiO2, as the top layer with various thickness and the second layer that contains fluorescence material, such as fluorescence dye or quantum dot, as well as scattering particles such as intralipid or TiO2. By measuring multiple spots with varying depth, the fluorescence signal as a function of the depth of fluorescence layer is obtained. The fluorescence intensity profile as a function of depth is obtained. If the distance to the first layer from the optical probe is not uniform, distance correction may be performed. Based on the plot of the measurement, fitting model ƒdepth(x) as a function of depth (x) can be obtained. For example, exponential model such as f(x)=a*exp(b*x)+ c*exp(d*x) may be used to achieve smaller fitting error; then the correction function for fluorescence intensity is obtained as $g_{depth}(x)=1/f(x)$.

Segmentation of the lumen and the border between the top layer and the second fluorescence layer can be processed automatically by the software algorithm. At the frame of interest for correcting fluorescence, edge detection provides the coordinates of the lumen and the border between the top layer and the second fluorescence layer.

In another embodiment, the border between the top layer and the second fluorescence layer can be defined semi-automatically by first segmentation performed by the software and further adjustment of the segmentation contour based on user input.

In another embodiment, the border between the top layer and the second fluorescence layer can be defined manually using user input to define the border contour. The depth is calculated from the coordinates of the lumen and the border.

Figure 8:
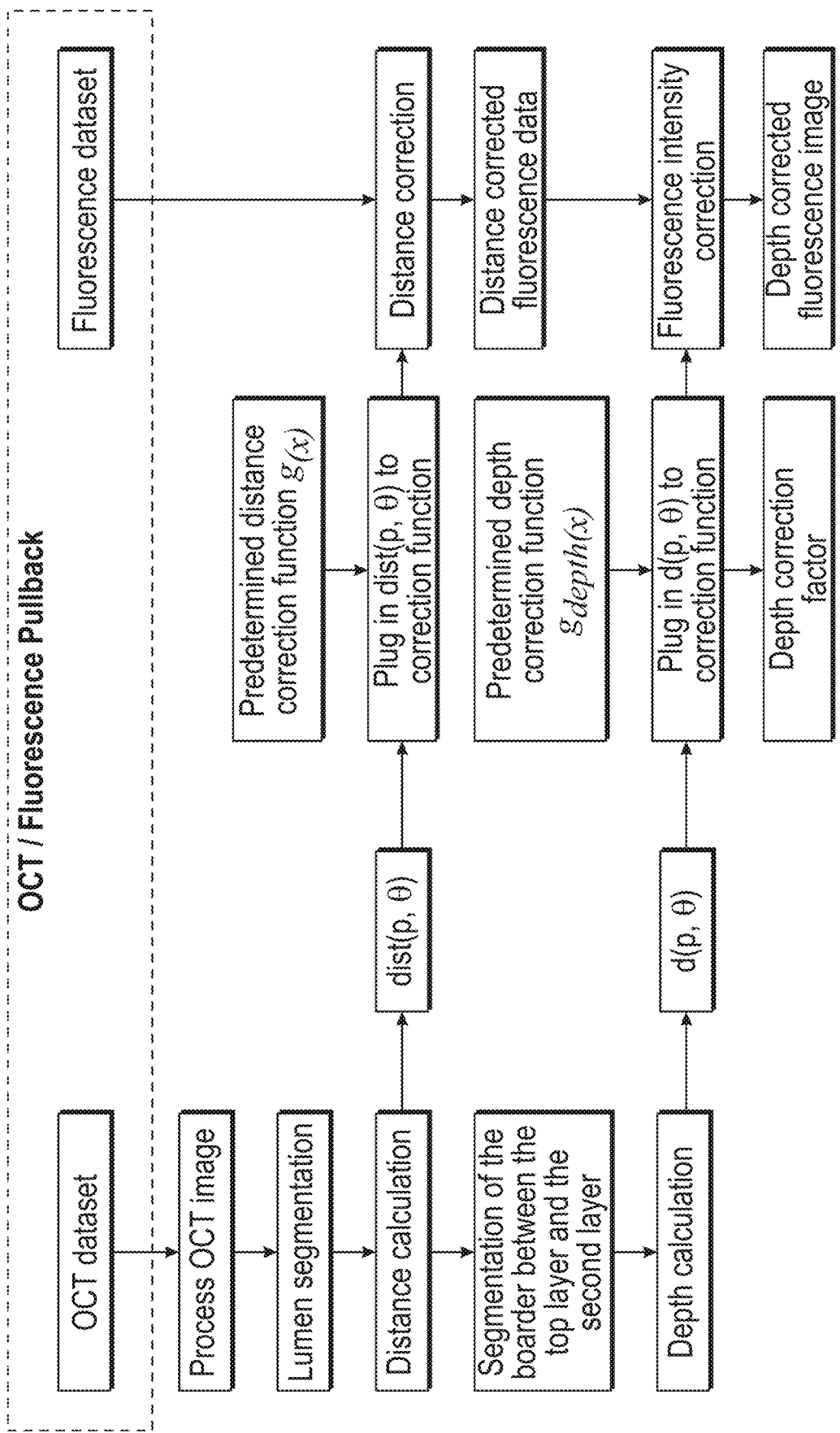
FIG. 8 provides a flowchart of the signal processing algorithm, according to one or more embodiment of the subject apparatus, method or system.

In yet another embodiment, fluorescence intensity is first corrected for the distance from optical probe to the luminal surface, then further corrected for the fluorescence intensity for the depth of the fluorescence layer. FIG. 8 shows the exemplary flowchart of this embodiment. The OCT dataset and fluorescence dataset are acquired simultaneously using a single catheter. The distance between the catheter and the fluorescence object are calculated from the OCT data as dist(p, θ). By imputing in the distance between the catheter and the fluorescence object, to the predetermined correction function, distance correction factor is determined. The fluorescence dataset is then corrected. Secondly, segmentation of the border between the top layer and the second layer is processed and the depth of the second layer is calculated as d(p, θ).

By imputing the depth value to the predetermined correction function, depth correction factor is determined. Distance corrected fluorescence data is depth-corrected by multiplying depth correction factor. In addition, since attenuation coefficient of the first layer over the fluorescence component may affect the fluorescence attenuation profile, attenuation coefficient can be used as a part of the correction algorithm in another embodiment.

Figure 9:
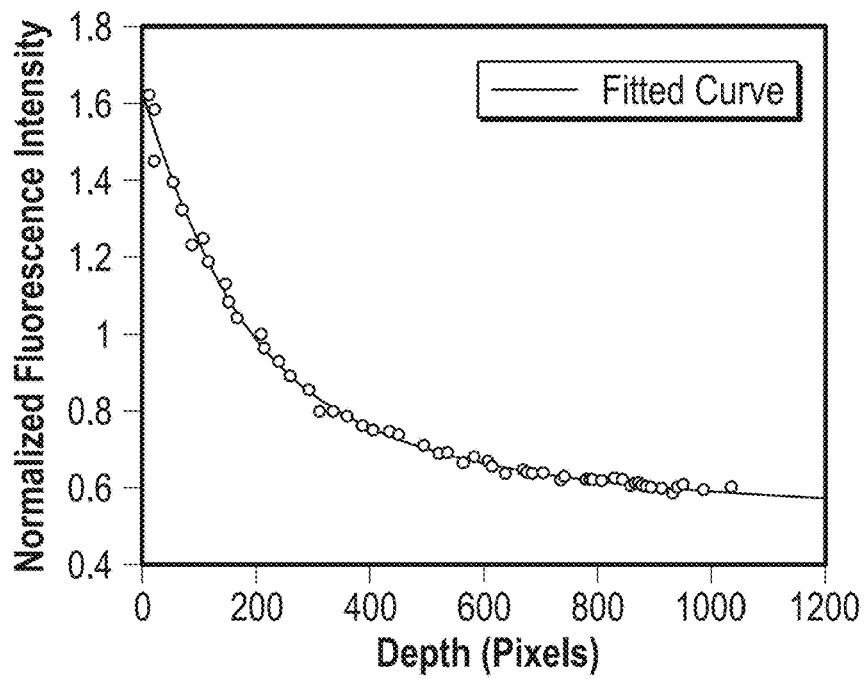
FIG. 9 is a chart depicting the fluorescence intensity as a function of depth, according to one or more embodiment of the subject apparatus, method or system.

FIG. 9 illustrates the exemplary result of the fluorescence measurement using solid polyurethane fluorescence phantom containing uniformly dispersed TiO2 and Qdot705 with varying thickness of non-fluorescence layer containing TiO2 on top (Ph1). The data is used to construct the depth correction function of the present innovation. Ph1 was imaged with the catheter consisted of optical fiber probe having ball lens at the distal end to obtain the fluorescence intensity data at various non-fluorescence layer thickness. Fluorescence data is plotted as a function of the thickness of the non-fluorescence layer (depth of fluorescence layer) and the data was fitted using an exponential model $f_{depth}(x)$ =a'*exp(b'*x)+c'*exp(d'*x) (FIG. 9). Depth correction function was then obtained as $g_{depth}(x)=1/f(x)$.

A test phantom (Ph2) was fabricated to illustrate the subject innovation. A fluorescence solid polyurethane rod containing uniformly dispersed TiO2 and Qdot705 was covered with non-fluorescence solid polyurethane layer with varying thickness. Ph2 was imaged with the OCT-fluorescence catheter at a different position, providing OCT images and fluorescence images of the rod with different depth profiles (FIG. 10).

Figures 10A, 10B, 10C:
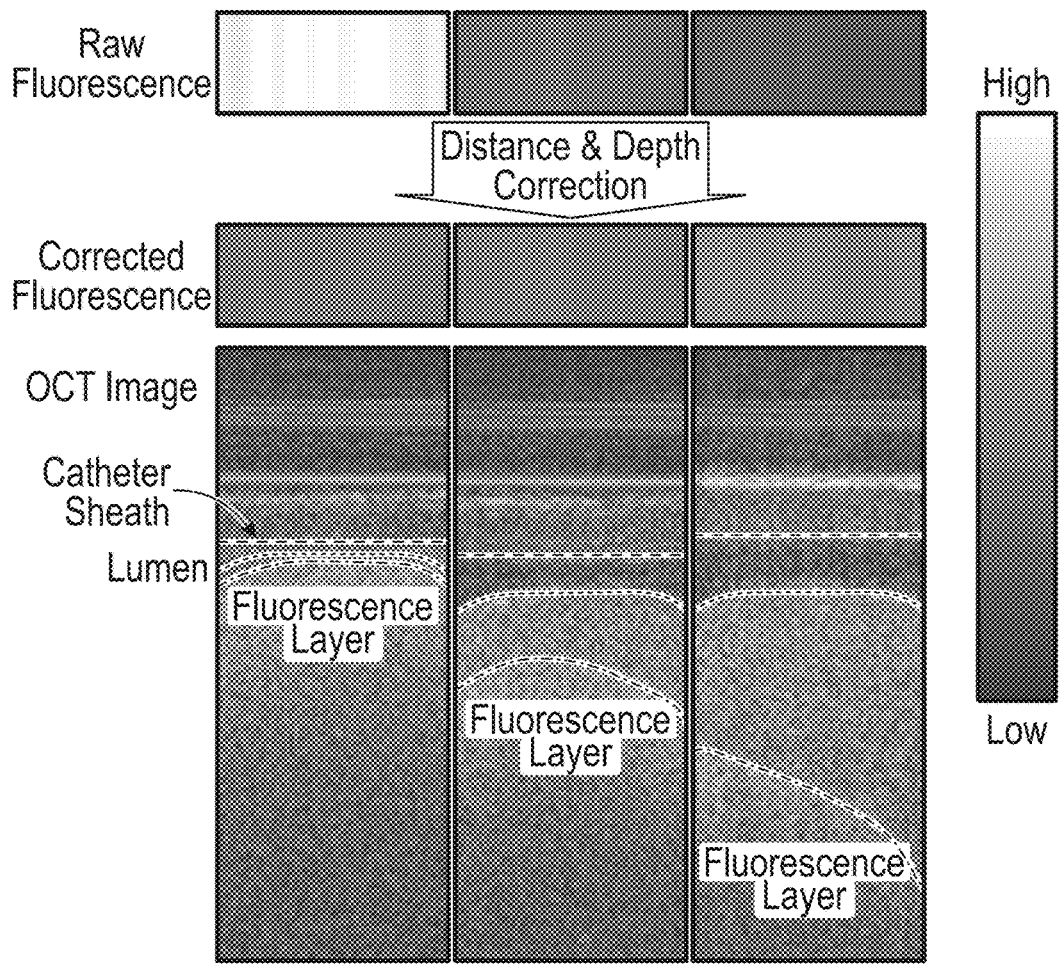
FIGS. 10a-10c provide images of exemplary results of the distance and depth correction of fluorescence, with FIG. 10a being raw fluorescence images, FIG. 10b providing distance and depth corrected OCT/fluorescence images.

As can be seen in FIG. 10a, the fluorescence intensity of the fluorescence rod at different depths shows significantly different fluorescence profiles. Fluorescence intensity was first corrected with the distance from optical probe to the phantom surface. Then, the depth of the fluorescence rod was measured by segmenting the border of the rod and the non-fluorescence layer. Using the depth value, the distance corrected fluorescence was further corrected with the depth. FIG. 10b shows the depth corrected fluorescence. By correcting the fluorescence for the distance and depth, the fluorescence profile of the fluorescence component under non-fluorescence layer shows similar fluorescence profile.

While the above disclosure describes certain illustrative embodiments, the invention is not limited to the above-described embodiments, and the following claims include various modifications and equivalent arrangements within their scope.

The invention claimed is:

1. A method of fluorescence calibration, comprising:
    providing an excitation light incident on an object through an optical probe;
    detecting a fluorescence light generated from the object;
    acquiring structural data of the object;
    calculating an optical attenuation property of the object based on the structural data; and
    calibrating fluorescence intensity based on the optical attenuation property and a depth calibration factor.

2. The method according to claim 1, further comprising calibrating the fluorescence intensity based on a distance between the optical probe and the object.

3. The method according to claim 1, further comprising calculating a distance between the optical probe and the object.

4. The method according to claim 1, further comprising detecting the fluorescence light and acquiring the structural data simultaneously.

5. The method according to claim 1, wherein the fluorescence light and the structural data are delivered by a double clad fiber.

6. The method according to claim 5, wherein the structural data is delivered by a core of the double clad fiber, and the fluorescence light is delivered by a cladding of the double clad fiber.

7. The method according to claim 1, further comprising acquiring the structural data by optical coherence tomography.

8. The method according to claim 1, wherein the optical attenuation property includes attenuation coefficient of an OCT image.

9. The method according to claim 1, further comprising applying the calibrated fluorescence intensity for correcting a fluorescence image constructed by the fluorescence light.

10. A method of fluorescence calibration, comprising:
    providing an excitation light incident on an object through an optical probe;
    detecting fluorescence intensity of a fluorescence light generated from the object;
    acquiring structural data of the object;
    calculating a distance between the optical probe and the object;
    calibrating the fluorescence intensity based on the distance;
    wherein if the fluorescence intensity calibrated based on the distance is higher than a predetermined level, then calculating an optical attenuation property of the object is based on the structural data; and
    wherein if the fluorescence intensity calibrated based on the distance is higher than the predetermined level, then calibrating the fluorescence intensity of the fluorescence light based on the optical attenuation property and a depth calibration factor.

11. The method of claim 10, further comprising detecting the fluorescence light and obtaining the structural data simultaneously.

12. The method according to claim 10, wherein the fluorescence light and the structural data are delivered by a double clad fiber.

13. The method according to claim 10, wherein the structural data is delivered by a core of the double clad fiber, and the fluorescence light is delivered by a cladding of the double clad fiber.

14. The method according to claim 10, further comprising acquiring the structural data by optical coherence tomography (OCT).

15. The method according to claim 10, wherein the optical attenuation property includes attenuation coefficient of an OCT image.

16. The method according to claim 10, further comprising applying only the fluorescence intensity calibrated by a first calibration factor for correcting a fluorescence image constructed by the fluorescence light if the fluorescence intensity calibrated by the first calibration factor is not higher than the predetermined level.

17. The method according to claim 10, further comprising applying the fluorescence intensity calibrated by both a first calibration factor and a second calibration factor for correcting a fluorescence image constructed by the fluorescence light if the fluorescence intensity calibrated by the first calibration factor is higher than the predetermined level.

* * * * *